US009707169B2

(12) United States Patent
deLong et al.

(10) Patent No.: US 9,707,169 B2
(45) Date of Patent: Jul. 18, 2017

(54) COMPOSITIONS AND METHODS FOR INHIBITING HAIR GROWTH

(71) Applicant: Elise A. Olsen, Chapel Hill, NC (US)

(72) Inventors: Mitchell A. deLong, Chapel Hill, NC (US); Elise A. Olsen, Chapel Hill, NC (US)

(73) Assignee: Elise Olsen, Chapel Hill, NC (US)

( * ) Notice: Subject to any disclaimer, the term of this patent is extended or adjusted under 35 U.S.C. 154(b) by 0 days.

(21) Appl. No.: 14/605,674

(22) Filed: Jan. 26, 2015

(65) Prior Publication Data

US 2015/0258001 A1 Sep. 17, 2015

Related U.S. Application Data

(62) Division of application No. 13/387,744, filed as application No. PCT/US2010/043701 on Jul. 29, 2010, now abandoned.

(60) Provisional application No. 61/229,605, filed on Jul. 29, 2009.

(51) Int. Cl.
A61K 31/25 (2006.01)
A61K 8/64 (2006.01)
A61K 8/49 (2006.01)
A61K 8/69 (2006.01)
A61K 31/198 (2006.01)
A61K 31/215 (2006.01)
A61K 31/4439 (2006.01)
A61K 31/585 (2006.01)
A61K 31/7004 (2006.01)
A61K 45/06 (2006.01)
A61Q 5/08 (2006.01)
A61Q 7/00 (2006.01)
A61Q 7/02 (2006.01)
A61Q 19/02 (2006.01)
A61K 8/37 (2006.01)
A61Q 5/02 (2006.01)
A61Q 17/04 (2006.01)
A61Q 19/00 (2006.01)
A61Q 19/10 (2006.01)

(52) U.S. Cl.
CPC ............ A61K 8/64 (2013.01); A61K 8/37 (2013.01); A61K 8/49 (2013.01); A61K 8/69 (2013.01); A61K 31/198 (2013.01); A61K 31/215 (2013.01); A61K 31/4439 (2013.01); A61K 31/585 (2013.01); A61K 31/7004 (2013.01); A61K 45/06 (2013.01); A61Q 5/08 (2013.01); A61Q 7/00 (2013.01); A61Q 7/02 (2013.01); A61Q 19/02 (2013.01); A61K 2800/42 (2013.01); A61Q 5/02 (2013.01); A61Q 17/04 (2013.01); A61Q 19/00 (2013.01); A61Q 19/10 (2013.01)

(58) Field of Classification Search
None
See application file for complete search history.

(56) References Cited

U.S. PATENT DOCUMENTS

| | | | |
|---|---|---|---|
| 3,426,137 | A | 2/1969 | Philpitt et al. |
| 3,776,938 | A | 12/1973 | Bergstrom et al. |
| 4,011,262 | A | 3/1977 | Hess et al. |
| 4,024,179 | A | 5/1977 | Bindra et al. |
| 4,128,720 | A | 12/1978 | Hayashi et al. |
| 4,911,928 | A | 3/1990 | Wallach |
| 5,686,468 | A | 11/1997 | Cullinan |
| 5,770,226 | A | 6/1998 | Hughes, Jr. et al. |
| 5,834,014 | A | 11/1998 | Weiner et al. |
| 5,972,944 | A | 10/1999 | Antonucci et al. |
| 6,068,834 | A | 5/2000 | Kvalnes et al. |
| 6,375,948 | B1 | 4/2002 | Tsuji et al. |
| 6,441,033 | B1 | 8/2002 | Sharif et al. |
| 6,458,835 | B2 | 10/2002 | Atwal |
| 6,524,593 | B1 | 2/2003 | Yu et al. |
| 6,649,655 | B2 | 11/2003 | Sharif et al. |
| 6,824,786 | B2 | 11/2004 | Yu et al. |
| 6,969,509 | B2 | 11/2005 | Chaudhuri et al. |
| 7,115,659 | B2 | 10/2006 | Delong |
| 7,211,278 | B2 | 5/2007 | Tsuji et al. |
| 7,270,805 | B1 | 9/2007 | Shore et al. |
| 7,388,029 | B2 | 6/2008 | DeLong et al. |

(Continued)

FOREIGN PATENT DOCUMENTS

WO WO 87/00427 1/1987
WO WO 88/08295 11/1988

(Continued)

OTHER PUBLICATIONS

US 7,595,346, 09/2009, Lee et al. (withdrawn)
Al-8810 Product Information, Prod. No. A 3846, Sigma, pp. 1-2 (Jul. 2002).*
Sharif et al., "Agonist Activity of Bimatoprost, Travoprost, Latanoprost, Unoprostone Isopropyl Ester and Other Prostaglandin Analogs at the Cloned Human Ciliary Body FP Prostaglandin Receptor," J. Ocular Pharmacol. Therap. 18:313-324 (2002).*
Choi et al., "Promising alternative clinical uses of prostaglandin F2a analogs: Beyond the eyelashes," J. Am. Acad. Dermatol. 72:712-6 (2015).*

(Continued)

Primary Examiner — Julie Ha
Assistant Examiner — Kristina M Hellman
(74) Attorney, Agent, or Firm — Michael Best & Friedrich LLP

(57) ABSTRACT

A method for inhibiting hair growth in mammals using compositions containing FP receptor antagonists (e.g., prostaglandin F analogs that are block activation of the FP receptor). The compositions can be applied topically to the skin and/or hair. The compositions can arrest hirsutism or hypertrichosis, reverse hirsutism and hypertrichosis, and further prevent hair growth. These compositions can also be used to protect hair from chemical or radiation-induced alopecia or hair loss. These compositions can also be used to inhibit pigmentation of the hair or skin.

13 Claims, 1 Drawing Sheet

(56) References Cited

U.S. PATENT DOCUMENTS

| | | | |
|---|---|---|---|
| 7,407,987 | B2 | 8/2008 | deLong et al. |
| 7,521,530 | B2 | 4/2009 | Peri et al. |
| RE41,278 | E | 4/2010 | Yu et al. |
| 7,723,537 | B2 | 5/2010 | Harichian et al. |
| 7,727,980 | B2 | 6/2010 | Zhi et al. |
| 7,737,288 | B2 | 6/2010 | Wang et al. |
| 7,744,935 | B2 | 6/2010 | Castor |
| 7,754,253 | B2 | 7/2010 | LeLouarn |
| 7,868,032 | B2 | 1/2011 | Woodward et al. |
| 2003/0072726 | A1 | 4/2003 | Banister et al. |
| 2005/0222232 | A1 | 10/2005 | DeLong et al. |
| 2006/0034952 | A1 | 2/2006 | Kondhalkar |
| 2006/0099280 | A1 | 5/2006 | Shibuya et al. |
| 2006/0135422 | A1 | 6/2006 | Moskowitz |
| 2006/0211626 | A1 | 9/2006 | Peri et al. |
| 2006/0211659 | A9 | 9/2006 | Dalko et al. |
| 2006/0216254 | A1 | 9/2006 | Majmudar et al. |
| 2007/0004620 | A1 | 1/2007 | Jabbour et al. |
| 2007/0105827 | A1 | 5/2007 | Blizzard et al. |
| 2007/0246057 | A1 | 10/2007 | Muller |
| 2007/0254920 | A1 | 11/2007 | deLong et al. |
| 2007/0269418 | A1 | 11/2007 | Pedersen et al. |
| 2008/0096240 | A1 | 4/2008 | Woodward et al. |
| 2008/0145330 | A1 | 6/2008 | Kondhalkar |
| 2008/0255094 | A1 | 10/2008 | Page et al. |
| 2008/0268079 | A1 | 10/2008 | Charles nee Newsham et al. |
| 2009/0175812 | A1 | 7/2009 | Harichian et al. |
| 2010/0143267 | A1 | 6/2010 | Pertile et al. |
| 2010/0256385 | A1 | 10/2010 | Woodward et al. |
| 2012/0245205 | A1 | 9/2012 | DeLong et al. |
| 2015/0257997 | A1 | 9/2015 | deLong et al. |

FOREIGN PATENT DOCUMENTS

| | | |
|---|---|---|
| WO | WO 94/27563 | 12/1994 |
| WO | WO 94/27586 | 12/1994 |
| WO | WO 95/24181 | 9/1995 |
| WO | WO 95/24884 | 9/1995 |
| WO | WO 95/24885 | 9/1995 |
| WO | WO 98/33472 | 8/1998 |
| WO | WO 99/06050 | 2/1999 |
| WO | WO 99/36030 | 7/1999 |
| WO | WO 03/051325 | 6/2003 |
| WO | WO 03/082278 | 10/2003 |
| WO | WO 03/089001 | 10/2003 |
| WO | WO 03/104266 | 12/2003 |
| WO | WO 2005/085169 | 9/2005 |
| WO | WO 2006/031555 | 3/2006 |
| WO | WO 2006/106311 | 10/2006 |
| WO | WO 2006/125582 | 11/2006 |
| WO | WO 2008/102782 | 8/2008 |
| WO | WO 2010/009578 | 1/2010 |
| WO | WO 2010/015487 | 2/2010 |
| WO | WO 2010/053548 | 5/2010 |
| WO | WO 2010/059140 | 5/2010 |
| WO | WO 2010/063673 | 6/2010 |
| WO | WO 2010/063678 | 6/2010 |
| WO | WO 2010/066639 | 6/2010 |
| WO | WO 2011/014649 | 2/2011 |

OTHER PUBLICATIONS

Paus et al., "Pathobiology of chemotherapy-induced hair loss," Lancet 14:e50-e58 (2013).*

Balsari AL, Morelli D, Menard S, Veronesi U, Colnaghi MI. Protection against doxorubicininduced alopecia in rats by liposome-entrapped monoclonal antibodies. FASEB J 1994; 8(2):226-230.

Banga et al., "Hydrogelbased Iontotherapeutic Delivery Devices for Transdermal Delivery of Peptide/Protein Drugs", Pharm. Res., vol. 10 (5), pp. 697-702 (1993).

Botchkarev VA, Komarova EA, Siebenhaar F, Botchkareva NV, Komarov PG, Maurer M, et al. "p53 is essential for chemotherapy-induced hair loss." Cancer Res 2000; 60(18):5002-5006.

C. Liljebris, G. Selen, B. Resul, J. Sternschantz, and U. Hacksell, "Derivatives of 17-Phenyl-18, 19,20-trinorprostaglandin F2a. Isopropyl Ester: Potential Antiglaucoma Agents", Journal of Medicinal Chemistry, vol. 38 No. 2 (1995), pp. 289-304.

Chollet, et al., "Tocolytic effects of a selective FP receptor antagonist in rodent models reveals an innovative approach to the treatement of preterm labor" BMC Pregnancy and Childbirth 2007, 7 (Suppl 1 ): S 16.

Danilenko OM, Ring BD, Yanagihara D, Benson W, Wiemann B, Starnes CO, et al. "Keratinocyte growth factor is an important endogenous mediator of hair follicle growth, development, and differentiation: normalization of the nulnu follicular differentiation defect and amelioration of chemotherapy-induced alopecia." Am J Patho/1995; 147(1):145-54.

Davis ST, Benson BG, Bramson HN, Chapman DE, Dickerson SH, Dold KM, et al. "Prevention of chemotherapy-induced alopecia in rats by CDK inhibitors." Science 2001; 291 (5501): 134-137.

Davis ST, Benson BG, Bramson HN, Chapman DE, Dickerson SH, Dold KM, et al. "Retraction." Science 2002; 298(5602):2327.

Dowton et al., "Influence of Liposomal Composition on Topical Delivery of Encapsulated Cyclosporin A: I. An in vitro Study Using Hairless Mouse Skin", S.T.P. Pharma Sciences, vol. 3, pp. 404-407 (1993).

Extended European Search Report for Application 10805042.8 dated Nov. 27, 2012 (20 pages).

Ferry, "Theoretical Model of Iontophoresis Utilized in Transdermal Drug Delivery", Pharmaceutical Acta Helvetiae, vol. 70, pp. 279-287 (1995).

G. L. Bundy and F. H. Lincoln, "Synthesis of 17-Phenyi-18,19,20-Trinorprostaglandins: I. The PG Series", Prostaglandin, vol. 9 No. 1 (1975), pp. 1-4.

Gangarosa et al., "Modern Iontophoresis for Local Drug Delivery", Int. J. Pharm, vol. 123, pp. 159-171 (1995).

Green et al., "Iontophoretic Delivery of a Series of Tripeptides Across the Skin in vitro", Pharm. Res., vol. 8, pp. 1121-1127 (1991).

Griffin, et al. "Al-8810: A Novel Prostaglandin F2a Analog with Selective Antagonist Effects at the Prostaglandin F2a (FP) Receptor" The Journal of Pharmacology and Experimental Therapeutics 1999, 290(3):1278-1284.

Hussein AM, Jimenez JJ, McCall CA, Yunis M. "Protection from chemotherapy-induced alopecia in a rat model." Science 1990; 249(4976): 1564-1566.

Hussein AM, Stuart A, Peters WP. "Protection against chemotherapy-induced alopecia by cyclosporine A in the newborn rat model." Dermatology 1995; 190(3):192-196.

Hussein AM. "Interleukin 1 protects against 1-beta-D-arabinofuranosylcytosine-induced alopecia in the newborn rat model." Cancer Res 1991; 51 (12):3329-3330.

Hussein AM. "Protection against cytosine arabinoside-induced alopecia by minoxidil in a rat animal model." Int J Dermatol, 1995; 34(7):470-473.

Jadoul et al., "Quantification and Localization of Fentanyl and TRH Delivered by Iontophoresis in the Skin", Int. J. Pharm., vol. 120, pp. 221-228 (1995).

Jimenez JJ, Haung HS, Yunis AA "Treatment with lmuVert/N-acetylcysteine protects rats from cyclophosphamide/cytarabine-induced alopecia." Cancer Invest 1992; 10(4):271-276.

Jimenez JJ, Roberts SM, Mejia J, Mauro LM, Munson JW, Elgart GW, et al. "Prevention of chemotherapy-induced alopecia in rodent models." Cell Stress Chaperones 2008; 13(1):31-38.

Jimenez JJ, Wong GHW, Yunis AA. "Interleukin 1 protects from cytosine arabinosideinduced alopecia in a rat model" FASEB J 1991; 5(10):2456-2458.

Jimenez JJ, Yunis AA. "Protection from 1-beta-D-arabinofuranosylcytosine-induced alopecia by epidermal growth factor and fibroblast growth factor in the rat model." Cancer Res 1992; 52(2):413-5.

Malkinson et al. "Prostaglandin protect against murine hair injury produced by ionizing radiation or doxorubicin" J Invest Dematol 1993, 101(1 Suppl):135S-137S.

Mansberger et al. "Eyelash formation secondary to latanoprost treatment in a patient with alopecia" Arch Ophthalmol 2000, 118:718-719; p. 718.

(56) References Cited

OTHER PUBLICATIONS

O'Brien et al., "An Updated Review of its Antiviral Activity, Pharmacokinetic Properties and Therapeutic Efficacy", Drugs, vol. 37, pp. 233-309 (1989).
Olsen EA (editor): "Disorders of Hair Growth: Diagnosis and Treatment." New York, McGraw-Hill, 2003, and references cited therein.
P. W. Collins and S. W. Djuric, "Synthesis of Therapeutically Useful Prostaglandin and Prostacyclin Analogs", Chem. Rev. vol. 93 (1993), pp. 1533-1564.
Parry et al., "Acyclovir Bioavailability in Human Skin", J. Invest. Dermatol., vol. 98 (6), pp. 856-863 (1992).
Paus R, Handjiski B, Eichmuller S, Czarnetzki BM. "Chemotherapy-induced alopecia in mice—induction by cyclophosphamide, inhibition by cyclosporine-A, and modulation by dexamethasone." Am J Patho, 1994; 144(4):719-734.
PCT/US2010/043701 International Preliminary Report on Patentability dated Feb. 9, 2012 (8 pages).
PCT/US2010/043701 International Search Report and Written Opinion dated Dec. 7, 2010 (10 pages).
Rao et al., "Reverse Iontophoresis: Noninvasive Glucose Monitoring in vivo in Humans", Pharm. Res., vol. 12 (12), pp. 1869-1873 (1995).
Santi et al., "Drug Reservoir Composition and Transport of Salmon Calcitonin in Transdermal Iontophoresis", Pharm. Res., vol. 14 (1), pp. 63-66 (1997).
Santi et al., "Reverse Iontophoresis—Parameters Determining Electroosmotic Flow: I. pH and Ionic Strength", J. Control. Release, vol. 38, pp. 159-165 (1996).
Santi et al., "Reverse Iontophoresis—Parameters Determining Electroosmotic Flow: II. Electrode Chamber Formulation", J. Control. Release, vol. 42, pp. 29-36 (1996).
Sharif, et al., "Antagonists of FP Prostanoid Receptor-mediated Inositol Phosphates Generation: Comparison with Some Purported FP Antagonists" Journal of Pharmacy and Pharmacology vol. 52 Issue 12, pp. 1529-1539 (2000).
Shirai A, Tsunoda H, Tamaoki T, Kamiya T. "Topical application of cyclosporin A induces rapid-remodeling of damaged anagen hair follicles produced in cyclophosphamide administered mice." J Dermatol Sci 2001; 27(1):7-13.
Sredni B, Xu RH, Albeck M, Gafter U, Gal R, Shani A, et al. "The protective role of the immunomodulator AS 101 against chemotherapy-induced alopecia studies on human and animal models." Int J Cancer 1996; 65(1):97-103.
Supplemental European Search Report and Written Opinion for Application 10805042.8 dated Dec. 14, 2012 (20 pages).
Tanaka, H. "The effect of a synthetic 7-thiaprostaglandin E1 derivatie, TEI-6122, on monocyte chemoattractant protein-1 induced chemotaxis in THP-1 cells" Br J. Pharm. (1995) 116, 2298.
Thysman et al., "Human Calcitonin Delivery in Rats by Iontophoresis", J. Pharm. Pharmacal., vol. 46, pp. 725-730 (1994).
Tsuda T, Ohmori Y, Muramatsu H, Hosaka Y, Takiguchi K, Saitoh F, et al. "Inhibitory effect of M50054, a novel inhibitor of apoptosis, on anti-Fas-antibody-induced hepatitis and chemotherapy-induced alopecia." Eur J Pharmaco, 2001; 433(1):37-45.
United States Office Action for U.S. Appl. No. 13/387,744 dated Jun. 3, 2013 (16 pages).
Volpato et al., "Iontophoresis Enhances the Transport of Acyclovir through Nude Mouse Skin by Electrorepulsion and Electroosmosis", Pharm. Res., vol. 12 (11), pp. 1623-1627 (1995).
W. Bartman, G. Beck, U. Lerch, H. Teufel, and B. Scholkens, "Luteolytic Prostaglandin: Synthesis and Biological Activity", Prostaglandin, vol. 17 No. 2 (1979), pp. 301-311.
Wallach and Philippot, "New Type of Lipid Vesicle: Novasome®", Liposome Technology, vol. 1, pp. 141-156 (1993).
Johnstone et al., "Prostaglandin-induced hair growth," Survey of Ophthal. 47 (Supp. 1):S185-S202 (2002).
Uno et al., "Effect of latanoprost on hair growth in the bald scalp of the stump-tailed macaque: a pilot study," Acta Derm. Venereal. 82:7-12 (2002).
United States Office Action for U.S. Appl. No. 13/387,744 dated Jan. 6, 2014 (10 pages).
European Patent Office Action for Application No. 10805042.8 dated Jun. 4, 2014 (12 pages).
United States Patent Office Action for U.S. Appl. No. 13/387,744 dated Jul. 25, 2014 (9 pages).
United States Patent Office Action for U.S. Appl. No. 14/605,664 dated May 23, 2016 (17 pages).

\* cited by examiner

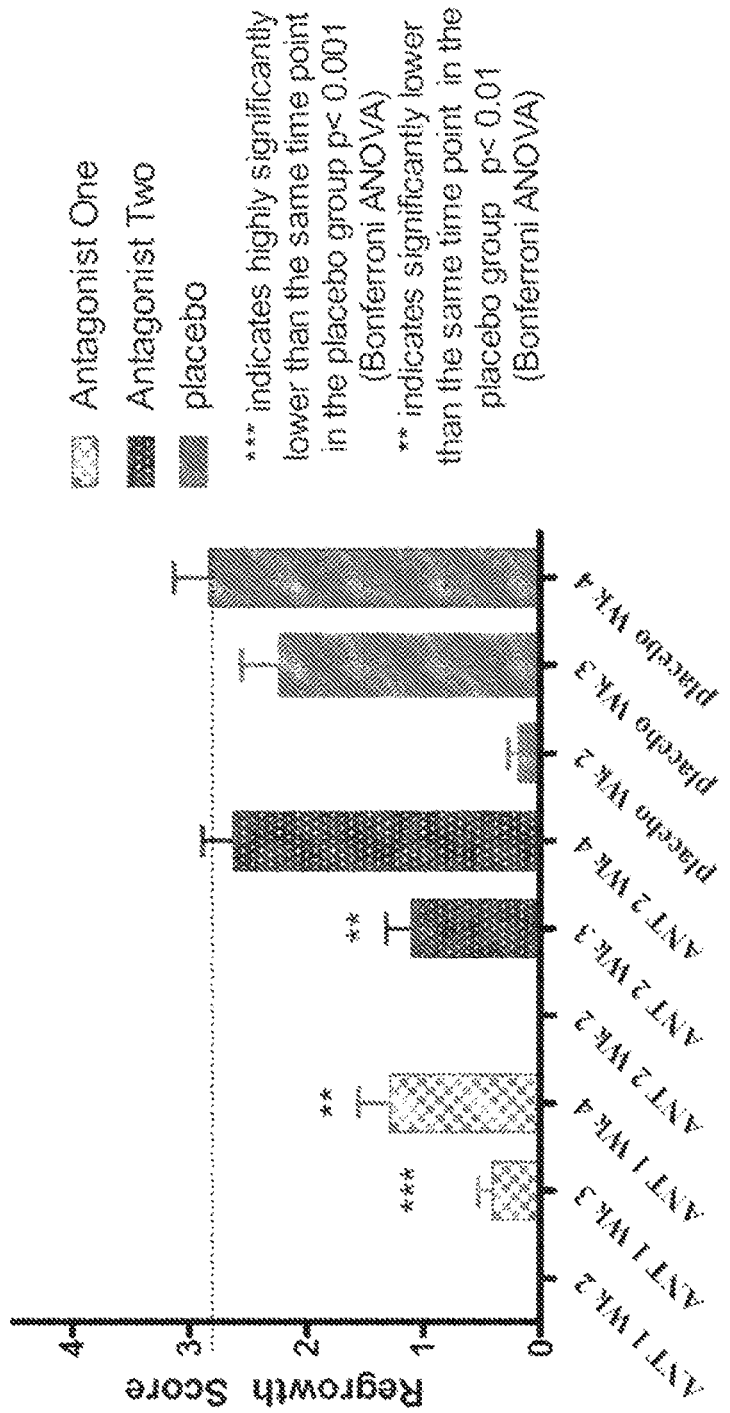

COMPOSITIONS AND METHODS FOR INHIBITING HAIR GROWTH

CROSS-REFERENCE TO RELATED APPLICATIONS

This application is a divisional of U.S. patent application Ser. No. 13/387,744, filed May 14, 2012, which is a national stage filing under 35 U.S.C. 371 of International Patent Application No. PCT/US2010/043701, filed Jul. 29, 2010, which claims priority to U.S. Provisional Patent Application No. 61/229,605, filed Jul. 29, 2009, the contents of all of which are incorporated herein by reference. Priority to these applications is hereby claimed.

FIELD OF THE INVENTION

This invention relates to compositions and methods for inhibiting hair growth and pigmentation in mammals. More particularly, this invention relates to compositions and methods for slowing or stopping the growth of hair, or both, for inhibiting hair growth to treat conditions such as hirsutism and hypertrichosis, for preventing chemotherapy or radiation-induced or related hair loss, and for inhibiting pigmentation in hair and skin.

BACKGROUND OF THE INVENTION

There are two main types of increased hair growth: (1) hirsutism, which is defined as the presence of excess terminal hair in women only and in anatomic sites where hair growth is considered to be a secondary male characteristic (i.e. beard, moustache, chest, and midline of lower abdomen primarily) and under androgen control and (2) hair density or length beyond the accepted limits of normal in a given body area for a particular age, race, and gender (hypertrichosis). Hypertrichosis may be in one or many areas and of terminal, vellus, or lanugo hair and is not under androgen control. Terminal hair is defined as hair that is similar in diameter to hair growing on the occipital scalp or eyebrows and usually >40 μm in diameter but its maximum length is body site dependent. Vellus and lanugo hair are of diminished diameter and color compared to terminal hair and do not grow beyond several centimeters in maximum length. Both types of increased hair growth can occur secondary to inherited conditions or can occur secondary to the use of certain medications. Hirsutism can be caused by the use of exogenous androgens or medications that bind to the androgen receptor (some progestins and anabolic steroids, for example) and diffuse hypertrichosis can be caused by the use of certain systemic drugs (minoxidil, diazoxide, cyclosporine, for example). Local hypertrichosis can be caused by the use of certain topical drugs, such as prostaglandin F analogs used for glaucoma and topical minoxidil used for hair growth in male or female pattern baldness. In addition, there are situations where the hair growth is determined to be within normal limits for a given ethnic group but increased in comparison with the general population. In some cases the excess hair growth can be desirable (i.e. in eyelashes) but in general, increased hair growth, especially in women, is viewed as undesirable and various means are utilized to remove the unwanted hair. There are also situations where the amount of hair is not indicative of hypertrichosis or hirsutism but the subject finds the amount of hair or the frequency of removal undesirable.

The current means of treating both hirsutism and hypertrichosis include physical means of hair removal including shaving, laser hair removal, electrolysis, depilatories, and waxing. These methods all require repetitive treatments, and none ensure complete and lasting hair removal, particularly in the presence of a continued systemic abnormality that is driving a vellus to terminal transition of hair. Currently, there is one FDA approved medication that slows hair growth: a topical omithine decarboxylase inhibitor Eflornithine (Vaniqa®) that shows significant efficacy in only a limited proportion of women with unwanted facial hair and has not been proven safe to use on other, larger body surface areas. There are several systemic agents that slow the transition of vellus to terminal hair growth or cause some miniaturization of terminal hair in women with hirsutism, and these agents include systemic antiandrogens (such as spironolactone, flutamide, and cyproterone acetate) and 5α-reductase inhibitors (such as finasteride or dutasteride). However, these agents do not cause total removal of the unwanted hair nor are they FDA approved for this indication. In addition, these systemic agents all have the risk of feminization of a male fetus in women of child-bearing potential and possibly other side effects as well. All of these methods, topical or systemic, require the continued use of other agents to remove unwanted hair. Thus there is a need for new products that work in a higher percentage of patients with unwanted hair, including those caused by hypertrichosis or hirsutism, and/or have fewer and less severe side effects.

Another unmet need is the alteration or prevention of pigmentation in the hair or skin. There are conditions where the skin may have too much pigmentation where inhibiting the pigmentation could be of value to patients. When used to alter or prevent pigmentation in the hair or skin, the compounds are applied in the same manner as for inhibition of hair growth, but the concentration or application may differ as needed.

Another unmet need is chemotherapy- or radiation-induced hair loss, particularly that occurring in women. Many cytotoxic chemotherapeutic agents or radiation that target rapidly growing cancer cells inadvertently also affect the rapidly growing anagen hair matrix cells, causing a profound and psychologically debilitating hair loss. This hair loss may make women in particular choose alternate therapies that do not cause this adverse effect, and/or it may cause a great deal of depression and/or anxiety during the entire cancer treatment process.

Prostaglandins have been shown in vivo to increase hair length and pigmentation. Naturally occurring prostaglandins (e.g., $PGA_2$, $PGB_2$, $PGE_1$, $PGE_2$, $PGF_{2\alpha}$, and $PGI_2$) are C-20 unsaturated fatty acids. $PGF_{2\alpha}$, the naturally occurring Prostaglandin F (PGF) analog in humans, is characterized by hydroxyl groups at the $C_8$ and $C_{11}$ positions on the alicyclic ring, a cis-double bond between $C_5$ and $C_6$, and a trans-double bond between $C_{13}$ and $C_{14}$. $PGF_{2\alpha}$ has the formula:

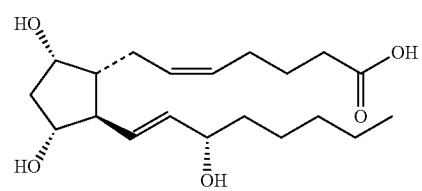 [SMILES: CCCCC[C@H](O)/C=C/[C@@H]1[C@@H](C/C=C\CCCC(=O)O)[C@@H](O)C[C@H]1O]

Analogs of naturally occurring Prostaglandin F are known in the art. For example, see U.S. Pat. No. 4,024,179 issued to Bindra and Johnson on May 17, 1977; German Patent No. DT-002,460,990 issued to Beck, Lerch, Seeger, and Teufel published on Jul. 1, 1976; U.S. Pat. No. 4,128,720 issued to Hayashi, Kori, and Miyake on Dec. 5, 1978; U.S. Pat. No. 4,011,262 issued to Hess, Johnson, Bindra, and Schaaf on Mar. 8, 1977; U.S. Pat. No. 3,776,938 issued to Bergstrom and Sjovall on Dec. 4, 1973: P. W. Collins and S. W. Djuric, "Synthesis of Therapeutically Useful Prostaglandin and Prostacyclin Analogs", Chem. Rev. Vol. 93 (1993), pp. 1533-1564; G. L. Bundy and F. H. Lincoln, "Synthesis of 17-Phenyl-18,19,20-Trinorprostaglandins: I. The PG Series". Prostaglandin, Vol. 9 No. 1 (1975), pp. 1-4; W. Bartman, G. Beck, U. Lerch, H. Teufel, and B. Scholkens, "Luteolytic Prostaglandin: Synthesis and Biological Activity", Prostaglandin, Vol. 17 No. 2 (1979), pp. 301-311; C. liljebris, G. Selen, B. Resul, J. Sternschantz, and U. Hacksell, "Derivatives of 17-Phenyl-18,19,20-trinorprostaglandin $F_2\alpha$. Isopropyl Ester: Potential Antiglaucoma Agents", *Journal of Medicinal Chemistry*, Vol. 38 No. 2 (1995), pp. 289-304.

Prostaglandins in general have a wide range of biological activities. For example, PGE2 has the following properties: a) regulator of cell proliferation, b) regulator of cytokine synthesis, c) regulator of immune responses and d) inducer of vasodilatation. Vasodilatation is thought to be one of the mechanisms of how minoxidil provides a hair growth benefit. In vitro results in the literature also indicate some anti-inflammatory properties of the prostaglandins. c.f.; Tanaka, H. Br J. Pharm. (1995) 116, 2298.

However, previous attempts at using prostaglandins to inhibit hair growth have been unsuccessful. Although different prostaglandin analogs can bind to multiple receptors at various concentrations, they have a biphasic effect. Further, the ability of the various in vitro animal models to predict human efficacy data has been poor. Certain animals have different receptors in different tissues, and even those that have similar receptor patterns may have different relative levels of receptors for prostaglandins. This makes evaluating the animal data to predict human efficacy challenging.

SUMMARY OF THE INVENTION

In certain embodiments, provided are methods of inhibiting hair growth, the method comprising administering to a subject a safe and effective amount of at least one FP receptor antagonist. Inhibiting hair growth may include slowing hair growth. Inhibiting hair growth may include stopping hair growth. The inhibition of hair growth may treat at least one of hirsutism, hypertrichosis, unwanted hair, chemotherapy-related hair loss, radiation-related hair loss, and a combination thereof. The FP receptor antagonist may be a compound of Formula I, II, III, IV, or V, as described below.

Further provided are methods of treating a condition, the method comprising administering to a subject a safe and effective amount of at least one FP receptor antagonist, wherein the condition is selected from at least one of hirsutism, hypertrichosis, unwanted hair, chemotherapy-related hair loss, radiation-related hair loss, hyperpigmentation, and a combination thereof. In certain embodiments, the condition is hirsutism, hypertrichosis, unwanted hair, chemotherapy-related hair loss, radiation-related hair loss, hyperpigmentation, and/or unwanted dark shade of hair. The FP receptor antagonist may be a compound of Formula I, II, III, IV, or V, as described below.

Further provided are methods of treating chemotherapy-related hair loss or radiation-related hair loss, the method comprising administering to a subject a safe and effective amount of at least one FP receptor antagonist. The FP receptor antagonist may be administered prior to chemotherapy or radiation, inhibit hair growth, and render the subject less susceptible to chemotherapy-related hair loss or radiation-related hair loss. The FP receptor antagonist may be a compound of Formula I, II, III, IV, or V, as described below.

Further provided are methods of inhibiting pigmentation of hair, skin, or both, the method comprising administering to a subject a safe and effective amount of a FP receptor antagonist. Pigmentation of hair may be inhibited. Pigmentation of skin may be inhibited. The FP receptor antagonist may be a compound of Formula I, II, III, IV, or V, as described below.

Further provided are methods of lightening skin, the method comprising administering to a subject a safe and effective amount of a FP receptor antagonist. The FP receptor antagonist may be a compound of Formula I, II, III, IV, or V, as described below.

Further provided are methods of inhibiting chemotherapy-related hair loss or radiation-related hair loss, the method comprising administering to a subject a safe and effective amount of a FP receptor antagonist. The FP receptor antagonist may be a compound of Formula I, II, III, IV, or V, as described below.

Further provided are pharmaceutical compositions comprising an FP receptor antagonist, a carrier; and at least one activity enhancer selected from the group consisting of i) hair growth inhibitor, ii) skin lightening agent, iii) hirsutism treatment agent, iv) preventative of chemotherapy-related hair loss or radiation-related hair loss, and v) penetration enhancer. The FP receptor antagonist may be a compound of Formula I, II, III, IV, or V, as described below. The activity enhancer may be eflornithine, deoxyArbutin, or spironolactone.

BRIEF DESCRIPTION OF THE DRAWINGS

The figure is a graph of the regrowth score for hair in mice after 2, 3, and 4 weeks of treatment with compounds according to the invention.

DETAILED DESCRIPTION OF THE INVENTION

One object of this invention to provide methods for using prostaglandin antagonists to inhibit the growth of hair and to provide compositions that inhibit hair growth. It is a further object of the invention to provide a selection of appropriate prostaglandin FP antagonists that will inhibit hair growth, which may include preventing regrowth, and thus treat diseases and conditions marked by increased or unwanted growth of hair or to prevent hair loss that is caused by chemotherapy or radiation induced hair loss. A further object of the invention is to provide compositions for inhibiting pigmentation of skin and/or hair. This invention relates to compositions comprising FP receptor antagonists (e.g., prostaglandin F receptor antagonists) to treat hirsutism, hypertrichosis, unwanted hair, chemotherapy-induced or related hair growth, radiation-induced or related hair growth, inhibition of pigmentation of hair and/or skin in mammals, and/or unwanted dark shade of hair. Treatment includes arresting or slowing hair growth, or inhibiting pigmentation formation in the skin or hair. The prostaglandin antagonist may interact strongly with hair-selective receptors, such as the FP receptor. The prostaglandin analog may selectively inhibit activation of the FP receptor and not activate any other receptors that would negate the effect of inhibiting the FP receptor.

There are multiple ways of inhibiting the function of the FP receptor. A particularly thorough explanation of each of those ways is found in US patent application US 2007/0004620 A1, which is specifically incorporated into this application by way of reference, and each of those methods of inhibiting the activation of the FP receptor is specifically contemplated for the current use. To illustrate, some of the more useful methods are described below, but the lack of an illustration is not to be construed as a lack of specific contemplation.

Publications and patents are referred to throughout this disclosure. All U.S. patents and publications cited herein are hereby incorporated by reference.

All percentages, ratios, and proportions used herein are by weight unless otherwise specified.

In the description of the invention various embodiments and individual features are disclosed. As will be apparent to a person having ordinary skill in the art, all combinations of such embodiments and features are possible and can result in preferred embodiments of the invention.

Definition and Usage of Terms

The following is a list of definitions for terms, as used herein:

"Acyl group" means a monovalent group suitable for acylating a nitrogen atom to form an amide or carbamate or an oxygen atom to form an ester group. Preferred acyl groups include benzoyl, acetyl, tert-butyl acetyl, para-phenyl benzoyl, and trifluoroacetyl. More preferred acyl groups include acetyl and benzoyl. The most preferred acyl group is acetyl.

"Aromatic group" means a monovalent group having a monocydclic ring structure or fused bicyclic ring structure. Monocyclic aromatic groups contain 5 to 10 carbon atoms, preferably 5 to 7 carbon atoms, and more preferably 5 to 6 carbon atoms in the ring. Bicyclic aromatic groups contain 8 to 12 carbon atoms, preferably 9 or 10 carbon atoms in the ring. Aromatic groups are unsubstituted. The most preferred aromatic group is phenyl.

"Carbocyclic group" means a monovalent saturated or unsaturated hydrocarbon ring. Carbocyclic groups are monocyclic, or are fused, spiro, or bridged bicyclic ring systems. Monocyclic carbocyclic groups contain 4 to 10 carbon atoms, preferably 4 to 7 carbon atoms, and more preferably 5 to 6 carbon atoms in the ring. Bicyclic carbocydic groups contain 8 to 12 carbon atoms, preferably 9 to 10 carbon atoms in the ring. Carbocyclic groups are unsubstituted. Preferred carbocyclic groups include cyclopentyl, cyclohexyl, cyclohexenyl, cycloheptyl, and cyclooctyl. More preferred carbocyclic groups include cyclohexyl, cycloheptyl, and cyclooctyl. The most preferred carbocyclic group is cycloheptyl. Carbocyclic groups are not aromatic.

"FP receptor antagonist" means a compound or compounds that inhibit activation or function of FP receptors. FP receptor antagonists further include prostaglandin analogs that act as prostaglandin antagonists, specifically, PGF antagonists, FP receptor antagonists selectively inhibit activation of the FP receptor and may not activate any other receptors that would negate the effect of inhibiting the FP receptor.

"Halogen atom" means F, Cl, Br, or I. Preferably, the halogen atom is F, Cl, or Br; more preferably Cl or F; and most preferably F.

"Halogenated hydrocarbon group" means a substituted monovalent hydrocarbon group or a substituted carbocyclic group, wherein at least one substituent is a halogen atom. Halogenated hydrocarbon groups can have a straight, branched, or cyclic structure. Preferred halogenated hydrocarbon groups have 1 to 12 carbon atoms, more preferably 1 to 6 carbon atoms, and most preferably 1 to 3 carbon atoms. Preferred halogen atom substituents are Cl and F. The most preferred halogenated hydrocarbon group is trifluoromethyl.

"Heteroaromatic group" means an aromatic ring containing carbon and 1 to 4 heteroatoms in the ring. Heteroaromatic groups are monocyclic or fused bicyclic rings. Monocyclic heteroaromatic groups contain 5 to 10 member atoms (i.e., carbon and heteroatoms), preferably 5 to 7, and more preferably 5 to 6 in the ring. Bicyclic heteroaromatic rings contain 8 to 12 member atoms, preferably 9 or 10 in the ring. Heteroaromatic groups are unsubstituted. Preferred heteroaromatic groups include thienyl, thiazolo, purinyl, pyrimidyl. pyridyl, and furanyl. More preferred heteroaromatic groups include thienyl, furanyl, and pyridyl. The most preferred heteroaromatic group is thienyl.

"Heteroatom" means an atom other than carbon in the ring of a heterocyclic group or the chain of a heterogeneous group. Preferably, heteroatoms are selected from the group consisting of nitrogen, sulfur, and oxygen atoms. Groups containing more than one heteroatom may contain different heteroatoms.

"Heterocyclic group" means a saturated or unsaturated ring structure containing carbon and 1 to 4 heteroatoms in the ring. No two heteroatoms are adjacent in the ring. Heterocyclic groups are not aromatic. Heterocyclic groups are monocyclic, or are fused or bridged bicyclic ring systems. Monocyclic heterocyclic groups contain 4 to 10 member atoms (i.e., including both carbon atoms and at least 1 heteroatom), preferably 4 to 7, and more preferably 5 to 6 in the ring. Bicyclic heterocyclic groups contain 8 to 12 member atoms, preferably 9 or 10 in the ring. Heterocyclic groups are unsubstituted. Preferred heterocyclic groups include piperzyl, morpholinyl, tetrahydrofuranyl, tetrahydropyranyl, and piperdyl.

"Heterogeneous group" means a saturated or unsaturated chain containing 1 to 18 member atoms (i.e., including both carbon and at least one heteroatom). No two heteroatoms are adjacent. Preferably, the chain contains 1 to 12 member atoms, more preferably 1 to 6, and most preferably 1 to 4. The chain may be straight or branched. Preferred branched heterogeneous groups have one or two branches, preferably one branch. Preferred heterogeneous groups are saturated. Unsaturated heterogeneous groups have one or more double bonds, one or more triple bonds, or both. Preferred unsaturated heterogeneous groups have one or two double bonds or one triple bond. More preferably, the unsaturated heterogeneous group has one double bond. Heterogeneous groups are unsubstituted.

"Lower monovalent hydrocarbon group" means a monovalent hydrocarbon group having 1 to 6, preferably 1 to 4 carbon atoms. "Lower alkyl" means a hydrocarbon chain of 1-4 carbon atoms.

"Monovalent hydrocarbon group" means a chain of 1 to 18 carbon atoms, preferably 1 to 12, more preferably 1 to 6, and most preferably 1 to 4 carbon atoms. Monovalent hydrocarbon groups may have a straight chain or branched chain structure. Preferred monovalent hydrocarbon groups have one or two branches, preferably 1 branch. Preferred monovalent hydrocarbon groups are saturated. Unsaturated monovalent hydrocarbon groups have one or more double bonds, one or more triple bonds, or combinations thereof. Preferred unsaturated monovalent hydrocarbon groups have one or two double bonds or one triple bond; more preferred unsaturated monovalent hydrocarbon groups have one double bond.

"Pharmaceutically acceptable" means suitable for use in a human or other mammal.

"Safe and effective amount" means a quantity of a compound high enough to provide a significant positive modification of the subject's condition to be treated, but low enough to avoid serious side effects (at a reasonable benefit/risk ratio).

"Substituted aromatic group" means an aromatic group wherein 1 to 4 of the hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups, aromatic groups, substituted aromatic groups, or any combination thereof. More preferred substituents include halogen atoms, monovalent hydrocarbon groups, and substituted monovalent hydrocarbon groups. Preferred substituted aromatic groups include naphthyl. The substituents may be substituted at the ortho, meta, or para position on the ring, or any combination thereof. The preferred substitution pattern on the ring is ortho or meta. The most preferred substitution pattern is ortho.

"Substituted carbocyclic group" means a carbocyclic group wherein 1 to 4 hydrogen atoms bonded to carbon atoms in the ring have been replaced with other substituents. Preferred substituents include: halogen atoms, cyano groups, monovalent hydrocarbon groups, monovalent heterogeneous groups, substituted monovalent hydrocarbon groups, aromatic groups, substituted aromatic groups, or any combination thereof. More preferred substituents include halogen atoms and substituted monovalent hydrocarbon groups. Carbocyclic group does not include aromatic rings.

"Substituted heteroaromatic group" means a heteroaromatic group wherein 1 to 4 hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups, substituted heterogeneous groups, phenyl groups, phenoxy groups, or any combination thereof. More preferred substituents include halogen atoms, halogenated hydrocarbon groups, monovalent hydrocarbon groups, and phenyl groups.

"Substituted heterocyclic group" means a heterocyclic group wherein 1 to 4 hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups. substituted heterogeneous groups, halogenated hydrocarbon groups, phenyl groups, phenoxy groups, or any combination thereof. More preferred substituents include halogen atoms and halogenated hydrocarbon groups. Substituted heterocyclic groups are not aromatic.

"Substituted heterogeneous group" means a heterogeneous group, wherein 1 to 4 of the hydrogen atoms bonded to carbon atoms in the chain have been replaced with other substituents. Preferred substituents include halogen atoms, hydroxy groups, alkoxy groups (e.g., methoxy, ethoxy, propoxy, butoxy, and pentoxy), aryloxy groups (e.g., phenoxy, chlorophenoxy, tolyloxy, methoxyphenoxy, benzyloxy, alkyloxycarbonylphenoxy, and acyloxyphenoxy), acyloxy groups (e.g., propionyloxy, benzoyloxy, and acetoxy), carbamoyloxy groups, carboxy groups, mercapto groups, alkylthio groups, acylthio groups, arylthio groups (e.g., phenylthio, chlorophenylthio, alkylphenylthio, alkoxyphenylthio, benzylthio, and alkyloxycarbonylphenylthio), aromatic groups (e.g., phenyl and tolyl), substituted aromatic groups (e.g., alkoxphenyl, alkoxycarbonylphenyl, and halophenyl), heterocyclic groups, heteroaromatic groups, and amino groups (e.g., amino, mono- and di-alkylamino having 1 to 3 carbon atoms, methylphenylamino, methylbenzylamino, alkanylamido groups of 1 to 3 carbon atoms, carbamamido, ureido, and guanidino).

"Substituted monovalent hydrocarbon group" means a monovalent hydrocarbon group wherein 1 to 4 of the hydrogen atoms bonded to carbon atoms in the chain have been replaced with other substituents. Preferred substituents include halogen atoms; halogenated hydrocarbon groups; alkyl groups (e.g., methyl, ethyl, propyl, and butyl); hydroxy groups; alkoxy groups (e.g., methoxy, ethoxy, propoxy, butoxy, and pentoxy); aryloxy groups (e.g., phenoxy, chlorophenoxy, tolyloxy, methoxyphenoxy, benzyloxy, alkyloxycarbonylphenoxy, and acyloxyphenoxy); acyloxy groups (e.g., propionyloxy, benzoyloxy, and acetoxy); carbamoyloxy groups; carboxy groups; mercapto groups; alkylthio groups; acylthio groups; arylthio groups (e.g., phenylthio, chlorophenylthio, alkylphenylthio, alkoxyphenylthio, benzylthio, and alkyloxycarbonylphenylthio); aryl groups (e.g., phenyl, tolyl, alkoxyphenyl, alkoxycarbonylphenyl, and halophenyl); heterocyclyl groups; heteroaryl groups; and amino groups (e.g., amino, mono- and di-alkanylamino groups of 1 to 3 carbon atoms, methylphenylamino, methylbenzylamino, alkanylamido groups of 1 to 3 carbon atoms, carbamamido, ureido, and guanidino).

As used herein "hyperpigmented region" means a localized region having high melanin content. Examples of these include, but are not limited to age spots, lentigines, melasma, chloasma, freckles, photoaging pigmentation changes, post inflammatory hyperpigmentation, post-trauma hyperpigmentation, ultraviolet light-induced pigmented blemishes, sun-induced pigmented blemishes, suntan, and the like.

As used herein, "skin lightening" means decreasing melanin in skin, including one or more of; overall lightening of basal skin tone, lightening of hyperpigmented regions including age spots, lentigines, melasma, chloasma, freckles, photoaging pigmentation changes, post inflammatory hyperpigmentation, suntan, ultraviolet light-induced pigmented blemishes, or sun-induced pigmented blemishes.

Compositions of the Invention

In one aspect, this invention relates to a composition for treating hirsutism, hypertrichosis, or unwanted hair in mammals. Treating any of these types of increased hair growth includes arresting hair growth or reversing the vellus or lanugo to terminal hair growth transformation, suppressing the hair growth rate, or preventing regrowth after hair removal. This invention also relates to a composition for preventing chemotherapy or radiation induced or related hair loss in mammals. Treatment of this condition includes arresting anagen hair growth to prevent the temporary effect of chemotherapy or radiation on the hair follicle. This invention also relates to a composition for inhibiting the formation of pigment in the skin and/or hair, including hyperpigmented regions, or skin lightening. The composition comprises A) an FP receptor antagonist or a selective modifier of the FP ligand as described herein and B) a carrier. The composition may further comprise C) one or more optional activity enhancers.

Preferably, A) the FP receptor antagonist is an active ingredient formulated into a composition, such as a pharmaceutical or cosmetic composition, administered for treatment or prophylaxis of a condition, including, for example, hirsutism, hypertrichosis, unwanted hair, chemotherapy-related hair loss, radiation-related hair loss, and pigmentation of the hair and/or skin. Standard pharmaceutical formulation techniques are used, such as those disclosed in Remington's Pharmaceutical Sciences, Mack Publishing Company, Easton, Pa. (1990).

Component A) can be a PGF analog having the structure of general Formula I:

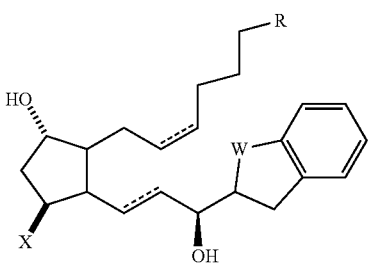

(I)

or structure according to general Formula II:

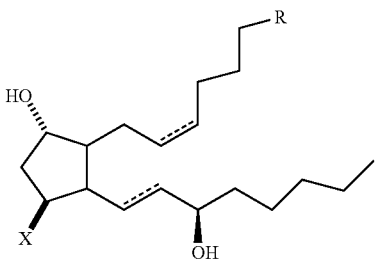

(II)

wherein R is selected from the group consisting of $CO_2H$, $C(O)NHOH$, $CO_2R_1$, $CH_2OH$, $S(O)_2R_1$, $C(O)NHR_1$, $P(O)(OR_1)R_2$, $C(O)NHS(O)_2R_1$, and tetrazole. $R_1$ and $R_2$ are independently selected from the group consisting of a hydrogen atom or a monovalent hydrocarbon groups, substituted monovalent hydrocarbon groups, aromatic groups, substituted aromatic groups, carbocyclic groups, substituted carbocyclic groups, heterogeneous groups, substituted heterogeneous groups, heterocyclic groups, substituted heterocyclic groups, heteroaromatic groups, and substituted heteroaromatic groups. Preferably, $R_1$ and $R_2$ are selected from the group consisting of $CH_3$, $C_2H_5$, and $C_3H_7$. Preferably, R is selected from the group consisting of $CO_2H$, $CO_2CH_3$, $C(O)NHC_2H_5$, $CO_2C_2H_5$, $CO_2C_3H_7$, $CO_2C_4H_9$, $CO_2C_3H_7O_2$, and $C(O)NHS(O)_2R_1$. More preferably, R is selected from the group consisting of $CO_2H$, $CO_2CH_3$, $CO_2C_2H_5$, $C(O)NHC_2H_5$ and $CO_2C_3H_7$. Most preferably, R is selected from the group consisting of $CO_2H$, $CO_2CH_3$, $C(O)NHC_2H_5$ and $CO_2C_3H_7$.

W is $-CH_2-$, $-O-$, or $-S(O)_2-$. In certain embodiments, W is $-CH_2-$.

X is halogen, lower alkyl, alkoxy, or hydrogen. In certain embodiments, X is methoxy or methyl. In certain embodiments, X is F.

An example of compounds according to general Formula I or II may include 11-deoxy-16-fluoro $PGF_{2\alpha}$ analogs such as AL-3138.

PGF analogs may be synthesized by methods known by one of skill in the art. PGF analogs may be purchased commercially, for example, from Cayman Chemicals (Ann Arbor, Mich.).

Examples of compounds according to Formula I or II may include the following:

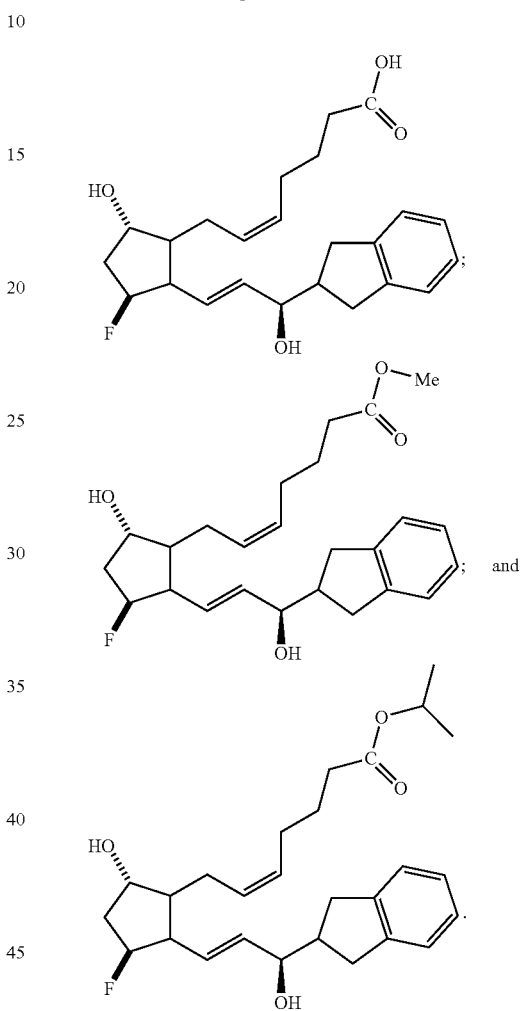

In other embodiments, compounds useful in the methods according to the invention may be of general Formula III:

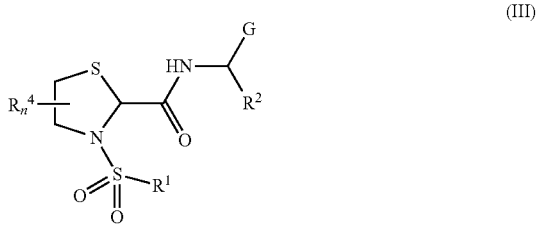

(III)

wherein G is selected from the group consisting of substituted or unsubstituted $C_1$-$C_6$-alkyl aryl, substituted or unsubstituted $C_1$-$C_6$-alkyl heteroaryl, substituted or unsubstituted $C_1$-$C_6$-alkyl cycloalkyl, substituted or unsubstituted $C_1$-$C_6$alkyl heteroaryl, substituted or unsubstituted aryl, substituted or unsubstituted heteroaryl, substituted or unsubstituted $C_3$-$C_8$-cycloalkyl or -heterocycloalkyl, said cycloalkyl or aryl or heteroaryl groups may be fused with cycloalkyl or aryl or heteroaryl groups;

$R^1$ is selected from the group consisting of substituted or unsubstituted aryl, substituted or unsubstituted heteroaryl, substituted or unsubstituted $C_3$-$C_8$-cycloalkyl or $C_3$-$C_8$-heterocycloalkyl, said (hetero)cycloalkyl or aryl or heteroaryl groups may be fused with (hetero)-cycloalkyl or aryl or heteroaryl groups;

$R^2$ is H, carboxy, acyl, alkoxycarbonyl, aminocarbonyl, substituted or unsubstituted $C_1$-$C_5$-alkyl carboxy, substituted or unsubstituted $C_1$-$C_5$-alkyl acyl, substituted or unsubstituted $C_1$-$C_5$-alkyl alkoxycarbonyl, substituted or unsubstituted $C_1$-$C_5$-alkyl aminocarbonyl, substituted or unsubstituted $C_1$-$C_5$-alkyl acyloxy, substituted or unsubstituted $C_1$-$C_5$-alkyl acylamino, substituted or unsubstituted $C_1$-$C_5$-alkyl ureido, substituted or unsubstituted $C_1$-$C_5$-alkyl amino, substituted or unsubstituted $C_1$-$C_5$-alkyl alkoxy, substituted or unsubstituted $C_1$-$C_5$-alkyl sulfanyl, substituted or unsubstituted $C_1$-$C_5$-alkyl sulfinyl, substituted or un substituted $C_1$-$C_5$-alkyl sulfonyl, substituted or unsubstituted $C_1$-$C_5$-alkyl sulfonylamino, substituted or unsubstituted $C_1$-$C_5$-alkyl sulfonyloxy, substituted or unsubstituted $C_1$-$C_8$alkyl, substituted or unsubstituted $C_2$-$C_6$-alkenyl, substituted or unsubstituted $C_2$-$C_6$-alkynyl, substituted or unsubstituted aryl, substituted or unsubstituted heteroaryl, substituted or unsubstituted $C_3$-$C_8$-cycloalkyl, substituted or unsubstituted heterocycloalkyl, substituted or unsubstituted $C_1$-$C_8$-alkyl aryl, substituted or unsubstituted $C_2$-$C_6$-alkyl heteroaryl, substituted or unsubstituted $C_1$-$C_6$-alkyl cycloalkyl, substituted or unsubstituted $C_1$-$C_6$-alkyl heterocycloalkyl, substituted or unsubstituted $C_2$-$C_6$-alkenyl aryl, substituted or unsubstituted $C_2$-$C_6$-alkenyl heteroaryl, substituted or unsubstituted $C_2$-$C_6$-alkynyl aryl, or substituted or unsubstituted $C_2$-$C_6$-alkynyl heteroaryl;

alternatively, $R^2$ and G may form a $C_3$-$C_8$-cycloalkyl ring;

$R^4$ is selected from the group consisting of substituted or unsubstituted $C_1$-$C_6$-alkyl, substituted or unsubstituted $C_2$-$C_6$-alkenyl, or unsubstituted $C_2$-$C_6$-alkynyl;

and n is an integer from 0 to 2.

According to some embodiments, G is an aryl group, e.g., a substituted or unsubstituted phenyl, like a biphenyl.

An example of a compound according to general Formula III may include that of AS804872:

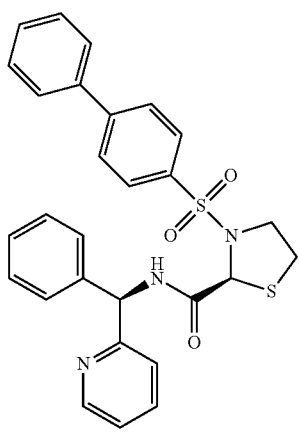

AS604872

In other embodiments, compounds useful in methods of inhibiting the activation of the FP receptor according to the invention may include compounds, peptides, and peptidomimetics disclosed in U.S. Pat. No. 7,521,530, which is incorporated herein by reference in its entirety. Compounds useful in the methods according to the invention may be of general Formula IV:

$$Y\text{-}AA_1\text{-}AA_2\text{-}AA_3\text{-}AA_4\text{-}AA_5\text{-}AA_6\text{-}AA_7\text{-}AA_8\text{-}Z \qquad (IV)$$

wherein Y is attached to the amino-terminus of said peptide and is selected from the group consisting of a hydrogen atom, an acetyl group, a benzoyl group, an acyl group (R—CO—), wherein R is a hydrophobic moiety, or an aroyl group (Ar—CO—), wherein Ar is an aryl group;

$AA_1$ and $AA_2$ are independently selected from the group consisting of no residue, isoleucine (Ile), leucine (Lou), and related alpha-amino acids possessing hydrophobic side-chains;

$AA_3$ is selected from the group consisting of no residue, glycine (Gly), alanine (Ala), and proline (Pro);

$AA_4$ is selected from the group consisting of histidine (His), phenylalanine (Phe). tyrosine (Tyr), tryptophan (Trp), and related alpha-amino acids possessing hydrophobic side-chains;

$AA_5$ is selected from the group consisting of arginine (Arg), omithine (Orn), lysine (Lys), citruline, 2-, 3-, and 4-pyridylalanine, and arginine surrogates;

$AA_6$ is selected from the group consisting of aspartic acid (Asp), asparagine (Asn), glutamic acid (Glu), glutamine (Gln), serine (Ser), 3-amino-5-phenylpentanoic acid, and Phe;

$AA_7$ is selected from the group consisting of no residue, Tyr, Phe, and related alpha-amino acids possessing hydrophobic side-chains, aromatic and arylalkyl amines, and aliphatic amines;

$AA_8$ is selected from the group consisting of no residue, Lys, Leu, Tyr, alpha-amino acids possessing hydrophobic side-chains, and aromatic and aliphatic amines; and Z is attached to the carboxy-terminus of said peptide and is selected from the group consisting of, a hydroxyl group, $NH_2$, and aromatic and aliphatic amines; and functional derivatives thereof.

An example of a compound according to general Formula IV is Ile-Leu-Gly-His-(citrulline)-Asp-Tyr-Lys (SEQ ID NO: 1), also known as THG113.31.

In other embodiments, compounds useful in the methods according to the invention may be of general Formula V:

$$Y\text{-}BTM\text{-}AA_1\text{-}AA_2\text{-}AA_3\text{-}Z \qquad (V)$$

wherein Y is attached to the amino-terminus of the peptide and is selected from the group consisting of a hydrogen atom, an acyl group (R—CO—), wherein R is a hydrophobic moiety, or an aroyl group (Ar—CO—), wherein Ar is an aryl group;

BTM (beta turn mimetic) is a dipeptide surrogate;

$AA_1$ is selected from the group consisting of Arg, Orn, Lys, citruline, 2-, 3-, and 4-pyridylalanine, and arginine surrogates;

$AA_2$ is selected from the group consisting of Asp, Asn, Glu, Gln, Ser, 3-amino-5-phenylpentanoic acid and Phe;

$AA_3$ is selected from the group consisting of no residue, Tyr, Phe, and related alpha-amino acids possessing hydrophobic side-chains, and aromatic amines, aliphatic amines and primary arylalkyl amines; and Z is selected from the group consisting of no residue, a hydroxyl group, $NH_2$, and aromatic, heteroaromatic and aliphatic amines; and functional derivatives thereof.

Compounds such as ((2S)-3-((1,1'-biphenyl)-4-ylsulfonyl)-N—((R)-phenyl(2-pyridinyl)methyl)-1,3-thiazolidine-2-carboxamide) are found in US Patent Application US 2008/0255094 A1 and international Patent Application WO 03/082278 A1, and are incorporated herein and specifically contemplated for this novel use of treating hirsutism, hypertrichosis, unwanted hair, chemotherapy-induced or related hair growth, radiation-induced or related hair growth, inhibition of pigmentation of hair and/or skin in mammals, and/or unwanted dark shade of hair. Compounds such as 11β-fluoro-15β-hydroxy PGF2α analogs, such as those disclosed in U.S. Pat. No. 6,649,655, which is incorporated by reference herein in its entirety, are useful and contemplated. In addition, peptides that inhibit FP activation by a different mechanism, such as those found in US Patent Application Publication No. US 2006/0211626 A1, are also useful and specifically contemplated, and pharmaceutically acceptable salts, hydrates, and biohydrolyzable amides, esters, and imides thereof are also suitable for component A).

Optical isomers, diastereomers, and enantiomers of the structure described above are also suitable as component A) of this invention. At all stereocenters where stereochemistry is not defined (i.e., $C_{11}$, $C_{12}$, $C_{15}$, and $C_{16}$), both epimers are envisioned.

Preferably, A) the FP receptor antagonist is an active ingredient formulated into a composition, such as a pharmaceutical or cosmetic composition, administered for treatment or prophylaxis of hirsutism, hypertrichosis, unwanted hair, chemotherapy-induced or related hair growth, radiation-induced or related hair growth, inhibition of pigmentation of hair and/or skin in mammals, and/or unwanted dark shade of hair. Standard pharmaceutical formulation techniques are used, such as those disclosed in Remington's Pharmaceutical Sciences, Mack Publishing Company, Easton, Pa. (1990).

The composition further comprises component B) a carrier. "Carrier" means one or more compatible substances that are suitable for administration to a mammal. Carrier includes solid or liquid filers, diluents, hydrotopes, surface-active agents, and encapsulating substances. "Compatible" means that the components of the composition are capable of being commingled with the FP receptor antagonist, and with each other, in a manner such that there is no interaction which would substantially reduce the efficacy of the composition under ordinary use situations. Carriers must be of sufficiently high purity and sufficiently low toxicity to render them suitable for administration to the mammal being treated. The carrier can be inert, or it can possess pharmaceutical benefits, cosmetic benefits, or both.

The choice of carrier for component B) depends on the route by which A) the FP receptor antagonist will be administered and the form of the composition. The composition may be in a variety of forms, suitable, for example, for systemic administration (e.g., oral, rectal, nasal, sublingual, buccal, or parenteral) or topical administration (e.g., local application on the skin, ocular, liposome delivery systems, or iontophoresis). Topical administration is preferred.

Carriers for systemic administration typically comprise one or more ingredients selected from the group consisting of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, combinations thereof, and others.

Component a) is a diluent. Suitable diluents include sugars such as glucose. lactose, dextrose, and sucrose; polyols such as propylene glycol; calcium carbonate; sodium carbonate; cellulose; glycerin, mannitol; and sorbitol.

Component b) is a lubricant. Suitable lubricants are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *theobroma*.

Component c) is a binder. Suitable binders include polyvinylpyrilidone; magnesium aluminum silicate; starches such as corn starch and potato starch; gelatin; tragacanth; and cellulose and its derivatives, such as sodium carboxymethylcellulose, ethyl cellulose, methylcellulose, and sodium carboxymethylcellulose.

Component d) is a disintegrant. Suitable disintegrants include starches, agar, alginic acid and the sodium salt thereof, effervescent mixtures, and croscarmelose.

Component e) is a colorant such as an FD&C dye.

Component f) is a flavor such as menthol, peppermint, and fruit flavors.

Component g) is a sweetener such as aspartame and saccharin.

Component h) is an antioxidant such as BHA, BHT, and vitamin E.

Component j) is a preservative such as methyl paraben and sodium benzoate.

Component k) is a glidant such as silicon dioxide.

Component m) is a solvent, such as water, isotonic saline, ethyl oleate, alcohols such as ethanol, and phosphate buffer solutions.

Component n) is a suspending agent. Suitable suspending agents include cellulose and its derivatives, such as methyl cellulose and sodium carboxymethyl cellulose; Avicel® RC-591 from FMC Corporation of Philadelphia, Pa.; tragacanth and sodium alginate.

Component o) is a wetting agent such as lecithin, polysorbate 80, and sodium lauryl sulfate.

Component p) is a surfactant such as the TWEENS® from Atlas Powder Company of Wilmington, Del.

Compositions for parenteral administration typically comprise A) 0.1 to 10% of a FP receptor antagonist and B) 90 to 99.9% of a carrier comprising a) a diluent, b) a lubricant, c) a binder, and m) a solvent. Preferably, component a) is propylene glycol, b) is sesame oil, c) is pyrrolidone, and m) is ethanol or ethyl oleate.

Compositions for oral administration can have various dosage forms. For example, solid forms include tablets, capsules, granules, and bulk powders. These oral dosage forms comprise a safe and effective amount, usually at least 5%, and preferably from 25% to 50%, of A) the FP receptor antagonist. The oral dosage compositions further comprise 8) 50 to 95% of a carrier, preferably 50 to 75%.

Tablets can be compressed, tablet triturates, enteric-coated, sugar-coated, film-coated, or multiple-compressed. Tablets typically comprise A) the FP receptor antagonist, and B) a carrier comprising ingredients selected from the group consisting of a) diluents, b) lubricants, c) binders, d) disintigrants, e) colorants, f) flavors, g) sweeteners, k) glidants, and combinations thereof. Preferred diluents include calcium carbonate, sodium carbonate, mannitol, lactose and cellulose. Preferred binders include starch, gelatin, and sucrose. Preferred disintegrants include starch, alginic acid, and croscarmelose. Preferred lubricants include magnesium stearate, stearic acid, and talc. Preferred colorants are the FD&C dyes, which can be added for appearance. Chewable tablets preferably contain g) sweeteners such as aspartame and saccharin, or f) flavors such as menthol, peppermint, and fruit flavors.

Capsules (including time release and sustained release formulations) typically comprise A) the FP receptor antagonist, and B) a carrier comprising one or more a) diluents disclosed above in a capsule comprising gelatin. Granules typically comprise A) the FP receptor antagonist, and preferably further comprise k) glidants such as silicon dioxide to improve flow characteristics.

The selection of ingredients in the carrier for oral compositions depends on secondary considerations like taste, cost, and shelf stability, which are not critical for the purposes of this invention. One skilled in the art would know how to select appropriate ingredients without undue experimentation.

The solid compositions may also be coated by conventional methods, typically with pH or time-dependent coatings, such that A) the FP receptor antagonist is released in the gastrointestinal tract in the vicinity of the desired application, or at various times to extend the desired action. The coatings typically comprise one or more components selected from the group consisting of cellulose acetate phthalate, polyvinylacetate phthalate, hydroxypropyl methyl cellulose phthalate, ethyl cellulose, EUDRAGIT® coatings (available from Rohm & Haas G.M.B.H. of Darmstadt, Germany), waxes and shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise A) the FP receptor antagonist and B) a carrier comprising ingredients selected from the group consisting of: a) diluents, e) colorants, and f) flavors, g) sweeteners, j) preservatives, m) solvents, n) suspending agents, and p) surfactants. Peroral liquid compositions preferably comprise one or more ingredients selected from the group consisting of e) colorants, f) flavors, and g) sweeteners.

Other compositions useful for attaining systemic delivery of the subject compounds include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethyl cellulose, and hydroxypropyl methyl cellulose. Such compositions may further comprise b) lubricants, e) colorants, f) flavors, g) sweeteners, h) antioxidants, and k) glidants.

The compositions may further comprise component C) an optional activity enhancer. Component C) may be selected from the group consisting of i) hair growth inhibitors (other than the PGF antagonists), ii) skin and/or hair lightening agents, iii) hirsutism treatment agents, iv) preventatives of chemotherapy- or radiation-induced or related alopecia or hair loss, and v) penetration enhancers, or combinations thereof. Components i)-iv) are exemplified by compounds that work marginally, if at all by itself, but can help the activity of the FP antagonist.

In certain embodiments, component C) is a i) hair growth inhibitor. Suitable hair growth inhibitors may include the following: advanced glycation end products (AGE's) and compounds such as lysine (WO2010063678A2, WO02010063673A2); extracts of *tetraselmis* species (US20100143267A1); fibroblast growth factor (FGF)18 (WO2008102782A1); cytotoxic lectin (US20080145330A1); trypsin and other enzymes (US20070269418A1); extract of *Juniperus* genus and/or malt extract (U.S. Pat. No. 8,375,948 and U.S. Pat. No. 7,211,278); hair growth-inhibiting active substances (WO06125582A1); extract of ginger root (US20060099280A1); toxalbumins such as ricin, abrin, or modeccin and the like (US20060034952A1); inhibitors of cysteine pathway enzymes (WO9524885A1); inhibitors of nitric oxide synthetase (WO9524884A1); ornithine amino transferase inhibitors (WO9524181A1); cyclooxygenase inhibitors such as NSAIDs (WO9427586A1); 5-lipoxygenase inhibitors (WO9427563A1) substances such as substituted guanidines or amidines (WO8808295A1); and aminobenzophenones (U.S. Pat. No. 3,426,137).

In certain embodiments, the hair growth inhibitor is eflornithine (Vaniqa®).

In certain embodiments, component C) is a ii) skin and/or hair lightening agent. Suitable skin lightening agents may include the following: acetylcholinesterase inhibitors (WO2010066639A2); terpenes (WO2010015487A3); *Phyllanthus emblica* fruit extract, *Bellis perennis* flower extract, and licorice root extract (WO2010059140A1); 4-methyl-7-hydroxycoumarin derived resorcinol derivatives (U.S. Pat. No. 7,723,537); 3-phenyl-chromen-4-one derivatives (WO2010009578A1); 3-dithiane resorcinol derivatives (US20090175812A1); goya or its extract and pine bark extracts (US20080268079A1); hydroquinone or its derivatives such as retinoids, azelaic acid, and N-acylbenzothiazolone compounds (U.S. Pat. No. 7,270,805); niacinamide, cucumber and lemon extracts, 2-imino-imidazolidin-4-one derivatives and phenyl derivatives (c.f., US20060216254A1); vasoconstrictors (WO06031555A2); Emblicanin A, Emblicanin B, Pedunculagin, Punigluconin, and flavonoids (U.S. Pat. No. 6,969,509); 4-substituted-7-hydroxycoumarin derived compounds (WO005085169A1); phenyl glycine derivatives (U.S. Pat. No. 6,824,786); skin lightening proteins, sulfobenzoic acids, and their derivatives (WO03051325A1); dihydroxybenzene derivatives (US20030072726A1); N-acetyl-aldosamines or N-acetylamino acids ((U.S. Pat. No. 6,524,593, reissued in 2010 as U.S. RE41278); and ellagic acid-based compounds, Kojic acid, salicylic acid, and the deoxyarbutins (U.S. Pat. No. 6,068,834, which is incorporated herein by reference in its entirety).

In certain embodiments, the skin lightening agent is deoxyArbutin or GirLite®.

In certain embodiments, component C) is a iii) hirsutism treatment agent. Suitable hirsutism treatment agents may include the following: botulinum toxin (U.S. Pat. No. 7,754,253); spironolactone (WO9936030A3, WO8700427A1); 2-phenyl-benzothiophene derivatives (U.S. Pat. No. 5,686,468); cyproterone acetate, flutamide, bicalutamide, and inhibitors of 5-alpha reductase such as finasteride dutasteride (U.S. Pat. Nos. 7,744,935, 7,737,288, 7,727,980); N,N-diethy-4-methyl-3-oxo-4-aza-5α-androstane-17β-carboxamide (4-MA, WO9906050A1); PTHR1 receptor ligands (WO2010053548A2); ketaconazole; estrogen receptor modulators such as oral contraceptives (U.S. Pat. No. 5,770,226); progesterone; estrogen (US20070105827); RU58841; neuropeptide Y receptor antagonists; thiazolidinedione derivatives such as rosiglitazone or pioglitazone (U.S. Pat. No. 5,972,944); biguanide (metformin) derivatives; cyoctol[6-(5-methoxy-1-heptyl)-bicyclo(3,3,0)octan-3-one]; botanicals including extracts of *Serenoa repens* (WO9833472A1); *Epilobium* species; *Cucurbite pepo* (U.S. Pat. No. 7,595,346); *Urtica dioica; Calluna vulgaris; Popu-*

*lus* species; *Barosma* species; and physical means of hair removal such as laser, electrolysis, and depilatory compounds.

In certain embodiments, the hirsutism treatment agent is oral spironolactone.

In certain embodiments, component C) is a iv) preventative of chemotherapy- or radiation-induced alopecia or hair loss. Suitable preventatives of chemotherapy- or radiation-induced alopecia or hair loss may include the following: 4-((cyanoimino((1,2,2-trimethylpropyl)amino)methyl) amino)benzonitrile (U.S. Pat. No. 6,458,835); growth factors including keratinocyte growth factor, epidermal growth factor, and fibroblast growth factor; prostaglandins including PGE2 and Misoprostol (U.S. Pat. Nos. 7,407,987, 7,388,029); ImuVert; AS101; IL-1; cyclin dependent kinases; p53 inhibitors; capase-3 inhibitors; acylated amino acids including N-acyl cysteine (US20060211659A9); nuclear hormone receptor ligands such as parathyroid hormone antagonist; vitamin and vitamin derivatives such as alphatocopherol; M50054; immunosuppressant agents especially cyclosporine; thermal treatments such as scalp hypothermia; angiotensin receptor blockers (US20060135422A1); and oral or topical minoxidil. For example, topical minoxidil has been shown to enhance regrowth after chemotherapy induced alopecia.

In certain embodiments, component C) is a v) penetration enhancer that can be added to all of the compositions for systemic administration except compositions for oral administration. The amount of component v), when present in the composition, is typically 1 to 5%. Examples of penetration enhancers include 2-methyl propan-2-ol, propan-2-ol, ethyl-2-hydroxypropanoate, hexan-2,5-diol, POE(2) ethyl ether, di(2-hydroxypropyl) ether, pentan-2,4-diol, acetone, POE(2) methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, POE ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl sallcylate, iso-propyl palmitate, ethyl laurate, 2-ethyl-hexyl pelargonate, iso-propyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hyroxyoctanoic acid, dimethyl sulphoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethy-m-toluamide, 1-dodecylazacyloheptan-2-one, and combinations thereof.

In certain embodiments of the invention, the FP receptor antagonists are topically administered. Topical compositions that can be applied locally to the skin may be in any form including solutions, oils, creams, ointments, gels, lotions, shampoos, leave-on and rinse-out hair conditioners, milks, cleansers, moisturizers, mousses, sprays, foam, skin patches, and the like. Topical compositions may comprise: component A) the FP receptor antagonists described above and component B) a carrier. The carrier of the topical composition may aid penetration of the FP receptor antagonists into the skin to reach the environment of the hair follicle. Component B) may further comprise one or more optional components. Topical compositions preferably further comprise C) one or more of the optional activity enhancers described above.

The exact amounts of each component in the topical composition depend on various factors. The amount of component A) depends on the binding affinity (IC50) of the FP receptor antagonist selected. The amount of component A) added to the topical composition is:

$$IC_{50} \times 10^{-1} \geq \% \text{ of component A}) \geq IC_{50} \times 10^{-5},$$

where $IC_{50}$ is expressed in nanomolar. For example, if the binding affinity of the FP receptor antagonist is 1 nM, the amount of component (A) will be 0.00001 to 0.1%. If the binding affinity of the FP receptor antagonist is 10 nM, the amount of component (A) will be 0.0001 to 0.1%. If the binding affinity of the FP receptor antagonist is 100 nM, the amount of component (A) will be 0.001 to 1.0%. If the binding affinity of the FP receptor antagonist is 1000 nM, the amount of component (A) will be 0.01 to 10%, preferably 0.1 to 5%. The amount and dosage of component A) are critical. If the amount of component A) is outside the ranges specified above (i.e., either higher or lower), efficacy of the treatment will be reduced, in the case of prodrugs such as the amide or ester of an FP receptor antagonist, the $IC_{50}$ of the free acid, or active form of the drug is to be used to determine its activity.

Component B) the carrier may comprise a single component or a combination of two or more components. Typical carriers for component B) in the topical compositions include water, alcohols, aloe vera gel, allantoin, glycerin, vitamin A and E oils, mineral oil, propylene glycol. PPG-2 myristyl propionate, dimethyl isosorbide, combinations thereof, and the like. Preferred carriers include propylene glycol, dimethyl isosorbide, and water.

The carrier of the topical composition may further comprise one or more ingredients selected from the group consisting of (q) emollients, (r) propellants, (s) solvents, (t) humectants, (u) thickeners, (v) powders, and (w) fragrances.

Ingredient (q) is an emollient. The amount of ingredient (q) in the topical composition is typically 5 to 95%. Suitable emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, polydimethylsiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Preferred emollients include stearyl alcohol and polydimethylsiloxane.

Ingredient (r) is a propellant. The amount of Ingredient (r) in the topical composition is typically 5 to 95%. Suitable propellants include propane, butane, iso-butane, dimethyl ether, carbon dioxide, nitrous oxide, and combinations thereof.

Ingredient (s) is a solvent. The amount of ingredient (s) in the topical composition is typically 5 to 95%. Suitable solvents include water, ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran, and combinations thereof. Preferred solvents include ethyl alcohol.

Ingredient (t) is a humectant. The amount of ingredient (t) in the topical composition is typically 5 to 95%. Suitable humectants include glycerin, sorbitol, sodium 2-pyrrolidone-5-carboxylate, soluble collagen, dibutyl phthalate, gelatin, and combinations thereof. Preferred humectants include glycerin.

Ingredient (u) is a thickener. The amount of ingredient (u) in the topical composition is typically 0 to 95%.

Ingredient (v) is a powder. The amount of ingredient (v) in the topical composition is typically 0 to 95%. Suitable powders include chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate, and combinations thereof.

Ingredient (w) is a fragrance. The amount of ingredient (w) in the topical composition is typically 0.001 to 0.5%, preferably 0.001 to 0.1%.

Component C) may be an activity enhancer is as described above. Any of the activity enhancers may be added to the topical compositions. In certain embodiments, the topical composition comprises 0.01 to 15% of at least one of components i)-iv). More preferably, the composition comprises 0.1 to 10%, and most preferably 0.5 to 5% of at least one of components i)-iv). In certain embodiments, the topical composition comprises 1 to 5% of component v).

In certain embodiments, pharmaceutical compositions may further comprise additional active agents including, but not limited to, sunscreens and sunblocks, anti-oxidants/radical scavengers, topical steroids, and retinoids.

In an alternative embodiment of the invention, pharmaceutical compositions for topical administration are prepared by conventional methods. Pharmaceutical compositions for topical administration typically comprise A) a FP receptor antagonist, B) a carrier, such as purified water, and one or more ingredients selected from the group consisting of (y) sugars such as dextrans, particularly dextran 70, (z) cellulose or a derivative thereof, (as) a salt, (bb) disodium EDTA (Edetate disodium), and (cc) a pH adjusting additive.

Examples of (z) cellulose derivatives suitable for use in the pharmaceutical composition for topical administration include sodium carboxymethyl cellulose, ethyl cellulose, methyl cellulose, and hydroxypropylmethylcellulose. Hydroxypropylmethylcellulose is preferred.

Examples of (aa) salts suitable for use in the for use in the pharmaceutical composition for topical administration include sodium chloride, potassium chloride, and combinations thereof.

Examples of (cc) pH adjusting additives include HCl or NaOH in amounts sufficient to adjust the pH of the pharmaceutical composition for topical administration to 5.2-7.5.

The FP receptor antagonists may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines. A preferred formulation for topical delivery of the present compounds uses liposomes as described in Dowton et al., "Influence of Liposomal Composition on Topical Delivery of Encapsulated Cyclosporin A: I. An in vitro Study Using Hairless Mouse Skin", S.T.P. Pharma Sciences, Vol. 3, pp. 404-407 (1993); Wallach and Philippot, "New Type of Lipid Vesicle. Novasome®", Liposome Technology. Vol. 1, pp. 141-156 (1993); Wallach, U.S. Pat. No. 4,911,928, assigned to Micro-Pak, Inc., issued Mar. 27, 1990; and Weiner et al., U.S. Pat. No. 5,834,014, assigned to The University of Michigan and Micro-Pak, Inc., issued Nov. 10, 1998 (with respect to Weiner et al., with a compound as described herein administered in lieu of, or in addition to, minoxidil).

The FP receptor antagonists may also be administered by iontophoresis. See, e.g., Banga et al., "Hydrogel-based Iontotherapeutic Delivery Devices for Transdermal Delivery of Peptide/Protein Drugs", Pharm. Res., Vol. 10 (5), pp. 697-702 (1993); Ferry, "Theoretical Model of Iontophoresis Utilized in Transdermal Drug Delivery", Pharmaceutical Acts Helvetiae, Vol 70, pp. 279-287 (1995); Gangarosa et al., "Modern Iontophoresis for Local Drug Delivery", Int. J. Pharm, Vol. 123, pp. 159-171 (1995); Green et al., "Iontophoretic Delivery of a Series of Tripeptides Across the Skin in vitro", Pharm. Res., Vol 8, pp. 1121-1127 (1991); Jadoul et al., "Quantification and Localization of Fentanyl and TRH Delivered by Iontophoresis in the Skin", Int. J. Pharm., Vol. 120, pp. 221-8 (1995); O'Brien et al., "An Updated Review of its Antiviral Activity, Pharmacokinetic Properties and Therapeutic Efficacy", Drugs, Vol. 37, pp. 233-309 (1989); Parry et al., "Acyclovir Bioavailability in Human Skin". J. Invest. Dermatol., Vol. 98 (8), pp. 856-63 (1992); Santi et al., "Drug Reservoir Composition and Transport of Salmon Calcitonin in transdermal Iontophoresis", Pharm. Res., Vol 14 (1), pp. 63-66 (1997); Santi et al., "Reverse Iontophoresis—Parameters Determining Electroosmotic Flow: I. pH and Ionic Strength", J. Control. Release, Vol. 38, pp. 159-165 (1996); Santi et al., "Reverse Iontophoresis—Parameters Determining Electroosmotic Flow: II. Electrode Chamber Formulation", J. Control. Release, Vol. 42, pp. 29-36 (1996); Rao et al., "Reverse Iontophoresis: Noninvasive Glucose Monitoring in vivo in Humans", Pharm. Res., Vol. 12 (12), pp. 1869-1873 (1995); Thysman et al., "Human Calcitonin Delivery in Rats by Iontophoresis", J. Pharm. Pharmacol., Vol. 46, pp. 725-730 (1994); and Volpato at al., "Iontophoresis Enhances the Transport of Acyclovir through Nude Mouse Skin by Electrorepulsion and Electroosmosis", Pharm. Res., Vol. 12 (11), pp. 1623-1627 (1995).

The FP receptor antagonists may be included in kits comprising a FP receptor antagonist, a systemic or topical composition described above, or both; and information, instructions, or both that use of the kit will provide treatment for conditions including, for example, hirsutism, hypertrichosis, unwanted hair, chemotherapy-related hair loss, radiation-related hair loss, and pigmentation of the hair and/or skin in mammals (particularly humans). The information and instructions may be in the form of words, pictures, or both, and the like. In addition, or in the alternative, the kit may comprise a FP receptor antagonist, a composition, or both; and information, instructions, or both, regarding methods of application of the FP receptor antagonist or composition, preferably with the benefit of inhibiting hair growth in mammals.

In all of the foregoing compositions, and for all routes of administration, the FP receptor antagonists can be used alone or in combinations of two or more FP receptor antagonists. The compositions may further comprise additional drugs or excipients as appropriate for the indication.

Methods of the Invention

This invention further relates to a method for inhibiting hair growth in mammals. The method comprises administering to a mammal (preferably a human) suffering from excess hair growth, a FP receptor antagonist described above. For example, a mammal diagnosed with hirsutism can be treated by the methods of this invention. A mammal diagnosed with hypertrichosis can be treated by the methods of this invention. A mammal with unwanted hair can be treated by the methods of this invention. Preferably, a systemic or topical composition comprising A) the FP receptor antagonist and B) a carrier is administered to the mammal. More preferably, the composition is a topical composition comprising A) the FP receptor antagonist. B) the carrier, and C) an optional activity enhancer.

This invention further relates to a method for treating chemotherapy-related or radiation-related hair loss. The methods may comprise administering to a subject (such as a mammal, preferably a human) a FP receptor antagonist described above. The FP receptor antagonist may be applied topically to the scalp, eyebrows, or eyelashes. The FP receptor antagonist may be applied prior to, during, and/or after chemotherapy or radiation treatment. The FP receptor antagonist may transiently inhibit the proliferation of the hair follicle matrix cells and inhibit hair growth, making the hair less susceptible to the effects of the cytotoxic agent or radiation. This in turn could help to prevent hair loss or slow the amount of hair loss from chemotherapy or radiation therapy. This could not only lead to greater compliance with a chemotherapy or radiation regimen that is a known cause of hair loss, but also would have dramatic effects on the psychological and emotional well being of patients with cancer going through chemotherapy or radiation.

This invention further relates to a method for inhibiting pigmentation of hair and/or skin and/or unwanted dark shade of hair. This invention further relates to a method for lightening hair and/or skin. The methods may comprise administering to a subject (such as a mammal, preferably a human) a FP receptor antagonist described above.

The dosage of the FP receptor antagonist administered depends on the method of administration. For systemic administration, (e.g., oral, rectal, nasal, sublingual, buccal, or parenteral), typically, 0.5 mg to 300 mg, preferably 0.5 mg to 100 mg, more preferably 0.1 mg to 10 mg, of a FP receptor antagonist described above is administered per day. These dosage ranges are merely exemplary, and daily administration can be adjusted depending on various factors. The specific dosage of the FP receptor antagonist to be administered, as well as the duration of treatment, and whether the treatment is topical or systemic are interdependent. The dosage and treatment regimen will also depend upon such factors as the specific FP receptor antagonist used, the treatment indication, the efficacy of the compound, the personal attributes of the subject (such as, for example, weight, age, sex, and medical condition of the subject), compliance with the treatment regimen, and the presence and severity of any side effects of the treatment.

For topical administration (e.g., local application on the skin, ocular, liposome delivery systems, or iontophoresis), the topical composition is typically administered from once per day up to four times per day. In general, 2-4 weeks is sufficient to observe a noticeable decrease in hair growth, and 6-10 weeks for a noticeable decrease in pigmentation.

EXAMPLES

These examples are intended to illustrate the invention to those skilled in the art and should not be interpreted as limiting the scope of the invention set forth in the claims.

Reference Example 1

Analytical Methods

FP receptor antagonists are tested for their potential to grow hair using the Telogen Conversion Assay. The Telogen Conversion Assay measures the potential of a FP receptor antagonist to inhibit the conversion of mice in the resting stage of the hair growth cycle ("telogen"), to the growth stage of the hair growth cycle ("anagen"), and to assess the rate of anagen growth.

Without intending to be limited by theory, there are three principal phases of the hair growth cycle: anagen, catagen, and telogen. It is believed that there is a longer telogen period in C3H mice (Harlan Sprague Dawley. Inc., Indianapolis, Ind.) from approximately 40 days of age until about 75 days of age, when hair growth is synchronized. It is believed that after 75 days of age, hair growth is no longer synchronized. Wherein about 40 day-old mice with dark fur (brown or black) are used in hair growth experiments, melanogenesis occurs along with hair (fur) growth wherein the topical application of hair growth inducers is evaluated. The Telogen Conversion Assay herein is used to screen FP receptor antagonists for potential hair growth by measuring melanogenesis and/or inhibition of expected hair growth.

Three groups of 44 day-old C3H mice are used: a vehicle control group, a positive control group, and a test FP receptor antagonist group, wherein the test FP receptor antagonist group is administered a FP receptor antagonist F used in the method of this invention. The length of the assay is typically 24 days with 16 treatment days (wherein the treatment days occur Mondays through Fridays). Day 1 is the first day of treatment. A typical study design is shown in Table 1 below. Typical dosage concentrations are set forth in Table 1, however the skilled artisan will readily understand that such concentrations may be modified.

TABLE 1

| Assay Parameters | | | | | |
|---|---|---|---|---|---|
| Group # | Animal # | Compound | Concentration | Application volume | Length of Study |
| 1 | 1-10 | Test Compound | 0.01% in vehicle** | 400 µL topical | 26 days |
| 2 | 11-20 | Positive Control (T3)* | 0.01% in vehicle** | 400 µL topical | 26 days |
| 3 | 21-30 | Vehicle** | N/A | 400 µL topical | 26 days |

*T3 is thyronine
**The vehicle is 60% ethanol, 20% propylene glycol, and 20% dimethyl isosorbide (commercially available from Sigma Chemical Co., St, Louis, MO).

The mice are treated topically Monday through Friday on their lower back (base of tail to the lower rib). A pipette and tip are used to deliver 400 µL to each mouse's back. The 400 µL application is applied slowly while moving hair on the mouse to allow the application to reach the skin.

While each treatment is being applied to the mouse topically, a visual grade of from 0 to 4 will be given to the skin color in the application area of each animal. As a mouse converts from telogen to anagen, its skin color will become more bluish-black. As indicated in Table 2, the grades 0 to 4 represent the following visual observations as the skin progresses from pink to bluish-black.

TABLE 2

| Evaluation Criteria | |
| --- | --- |
| Visual Observation | Grade |
| Pink Skin Color | 0 |
| Skin is light gray (indication of initiation of anagen) | 1 |
| Appearance of hair | 2 |
| Spots are aggregating to form one large haired area | 3 |
| Skin almost black with hair covering majority of treatment area (indication of mouse in full anagen) | 4 |

Example 1

An FP receptor antagonist having the structure:

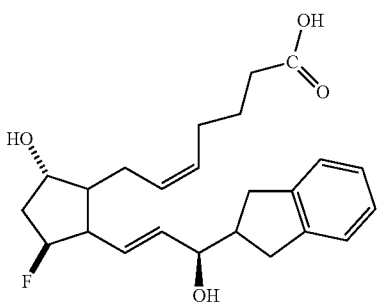 [SMILES: O=C(O)CCC/C=C\CC1C(/C=C/[C@H](O)C2Cc3ccccc3C2)[C@@H](F)C[C@@H]1O]

was tested according to the method of Reference Example 1. The average grade was calculated by averaging the grades of 7 mice after 23 days, 25 days, and 26 days. The results are in Table 3.

Example 2

An FP receptor antagonist having the structure:

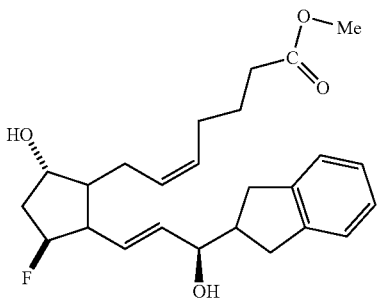 [SMILES: COC(=O)CCC/C=C\CC1C(/C=C/[C@H](O)C2Cc3ccccc3C2)[C@@H](F)C[C@@H]1O]

was tested according to the method of Reference Example 1. The average grade was calculated by averaging the grades of 7 mice after 23 days. The results are in Table 3.

TABLE 3

| | Average Grades | | |
| --- | --- | --- | --- |
| Example | 23 Days | 25 Days | 26 Days |
| 1 | 0.4 | 0.1 | 0.7 |
| 2 | 0.1 | not measured | not measured |

Example 3

An FP receptor antagonist having the structure:

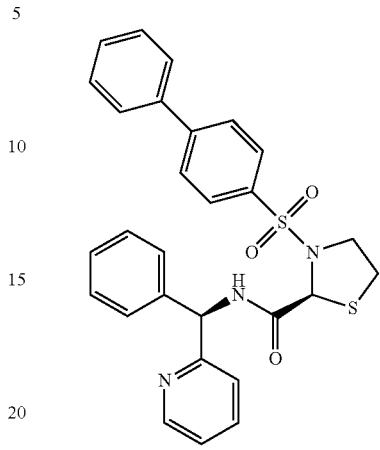

is tested according to the method of Reference Example 1. The average grade is calculated by averaging the grades of 7 mice after 23 days. The results show that the compound significantly reduces hair growth.

Example 4

An FP receptor antagonist having the structure:

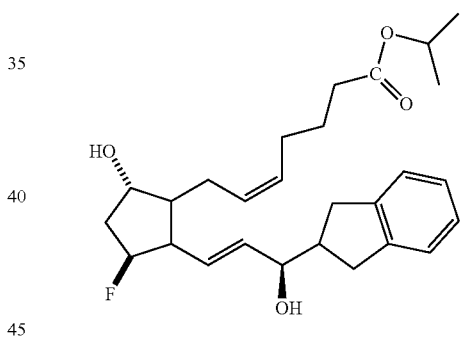

is tested according to the method of Reference Example 1. The average grade is calculated by averaging the grades of 7 mice after 23 days. The results show that the compound significantly reduces hair growth.

Example 5

An FP receptor antagonist comprising the peptide:

```
                                    (SEQ ID NO: 1)
     Ile-Leu-Gly-His-(citrulline)-Asp-Tyr-Lys
``` is tested according to the method of Reference Example 1. The average grade is calculated by averaging the grades of 7 mice after 23 days. The results show that the compound significantly reduces hair growth.

Example 6

Two FP receptor antagonists according to the invention (ANT 1, ANT 2) or placebo were applied daily to mice using the Telogen Conversion Assay, as described in Reference Example 1, to assess their ability to slow hair regrowth. ANT 1 is the compound of Example 2, and ANT 2 is the compound of Example 3. In this model, placebo-treated mice began to regrow hair by week two, with significant regrowth by week 4. As shown in the figure, both ANT 1 and ANT 2 at the appropriate dose-level, inhibited hair regrowth at week 3 and week 4 as compared to the control group.

Example 7

Compositions for topical administration are made, comprising:

| Component | 3-1 | 3-2 | 3-3 | 3-4 |
| --- | --- | --- | --- | --- |
| PGF antagonist (wt %) | 0.001 | 0.01 | 0.1 | 1.0 |
| $IC_{50}$ of the FP receptor antagonist (nM) | 1 | 10 | 100 | 1000 |
| Ethanol (wt %) | 59.99 | 59.9 | 59.4 | 54.0 |
| Propylene Glycol (wt %) | 20.00 | 20.0 | 19.8 | 18.0 |
| Dimethyl Isosorbide (wt %) | 20.66 | 20.0 | 19.8 | 18.0 |

A human subject suffering from hirsutism is treated by a method of this invention. Specifically, for 16 weeks, one of the above compositions is daily administered topically to the subject.

Example 8

A composition for topical administration is made according to the method of Dowton et al., "Influence of Liposomal Composition on Topical Delivery of Encapsulated Cyclosporin A: I. An in vitro Study Using Hairless Mouse Skin", S.T.P. Pharma Sciences, Vol. 3, pp. 404-407 (1993), using a PGF analog that is an antagonist of the FP receptor in lieu of cyclosporin A and using the NOVASOME® 1 (available from Micro-Pak, Inc. of Wilmington, Del.) for the non-ionic liposomal formulation. A human subject suffering from hirsutism is treated each day with the above composition. Specifically, for 16 weeks, the above composition is administered topically to the subject.

Example 9

Shampoos or body washes are made, comprising:

| Component | Ex. 6-1 | Ex. 6-2 | Ex. 6-3 | Ex. 6-4 |
| --- | --- | --- | --- | --- |
| Ammonium Lauryl Sulfate | 11.5% | 11.5% | 9.5% | 7.5% |
| Ammonium Laureth Sulfate | 4% | 3% | 2% | 2% |
| Cocamide MEA | 2% | 2% | 2% | 2% |
| Ethylene Glycol Distearate | 2% | 2% | 2% | 2% |
| Cetyl Alcohol | 2% | 2% | 2% | 2% |
| Stearyl Alcohol | 1.2% | 1.2% | 1.2% | 1.2% |
| Glycerin | 1% | 1% | 1% | 1% |
| Polyquaternium 10 | 0.5% | 0.25% | — | — |
| Polyquaternium 24 | — | — | 0.5% | 0.25% |
| Sodium Chloride | 0.1% | 0.1% | 0.1% | 0.1% |
| Sucrose Polyesters of Cottonate Fatty Acid | 3% | 3% | — | — |
| Sucrose Polyesters of Behenate Fatty Acid | 2% | 3% | — | — |
| Polydimethyl Siloxane | — | — | 3% | 2% |
| Cocaminopropyl Betaine | — | 1% | 3% | 3% |
| Lauryl Dimethyl Amine Oxide | 1.5% | 1.5% | 1.5% | 1.5% |
| Decyl Polyglucose | — | — | 1% | 1% |
| DMDM Hydantion | 0.15% | 0.15% | 0 15% | 0.15% |
| PGF antagonist having $IC_{50}$ of 10 nM | — | 0.2% | 0.2% | — |
| PGF antagonist having $IC_{50}$ of 100 nM | 1.0% | — | — | 1.0 |
| Vaniqa | — | — | 3% | 2% |
| Phenoxyethanol | 0.5% | 0.5% | 0.5% | 0.5% |
| Fragrance | 0.5% | 0.5% | 0.5% | 0.5% |
| Water | q.s. | q.s. | q.s. | q.s. |

A human subject suffering from hirsutism is treated by a method of this invention. Specifically, for 12 weeks, a shampoo or body-wash selected from the ones described above is used daily by the subject.

Example 10

Body washes are made according to Example 9. A human subject suffering from hypertrichosis is treated by a method of this invention. Specifically, for 12 weeks, a body-wash selected from the ones described above is used daily by the subject. A body-wash selected from the ones described above may be used by the subject daily for 12 weeks after laser hair removal to decrease the growth rate or growth of remaining hairs.

Example 11

Shampoos are made according to Example 9. A human subject suffering from chemotherapy-related or radiation-related hair loss is treated by a method of this invention. Specifically, for days to several weeks prior to chemotherapy or radiation through days to weeks after chemotherapy or radiation, a shampoo selected from the ones described above is used daily by the subject by applying to the scalp. Solution may also be applied to the eyebrows or eyelashes. The treatment reduces hair loss after chemotherapy or radiation treatment.

Example 12

Body washes are made according to Example 9. A human subject suffering from unwanted hair is treated by a method of this invention. Specifically, for 12 weeks, a body-wash selected from the ones described above is used daily by the subject. A body-wash selected from the ones described above may be used by the subject daily for 12 weeks after laser hair removal to decrease the growth rate or growth of remaining hairs.

Example 13

Methods for testing the prevention of chemotherapy-related alopecia are as follows:
1. Rats are treated with cytosine arabinoside and doxorubicin plus or minus the agent in question prior to injection of chloroleukemic cells.
2. Topical agent in question is applied to anagen test sites in B6D2F1 mice 2 hours prior to intraperitoneal doxorubicin.
3. C57BL/6 mice are treated with agent in question prior to cyclophosphamide.
4. Neonatal rat model is treated with topical application of agent in question prior to either etoposide or cytoxan-doxorubicin combination.

The method for testing the prevention of radiation induced alopecia is as follows: Mice with hair either synchronously in telogen or anagen (induced by plucking) are pretreated for 3 days with the agent in question prior to irradiation with 10-20 cGy and hair growth is compared to mice irradiated and not treated and non irradiated mice.

Example 14

Assays to Determine an FP Antagonist

The FP receptor is a well-described GPCR of 7-transmembrane domains. Assays to determine if a compound is an FP receptor agonist, antagonist, or not are well-known in the art. Examples are cited herein for illustrative purposes only and are not intended to be limiting. Both in vitro and in vivo assays are readily available. One standard in vivo assay is PanLabs' murine antinidatory assay in which pregnant mice are injected with the compound to be tested and then increasing amounts of the known murine-abortafacient. $PGF_{2\alpha}$, are injected and an $EC_{50}$ of protection from the effect of $PGF_{2\alpha}$ is calculated using a program such as GraphPad Prism.

Several in vitro assays are available (Sharif, et al., Antagonists of FP Prostanoid Receptor-mediated Inositol Phosphates Generation; Comparison with Some Purported FP Antagonists *Journal of Pharmacy and Pharmacology* Volume 52 Issue 12, Pages 1529-1539, incorporated herein by reference).

Agonist/antagonist assays are available from Ricerca Biosciences.

A mouse preterm parturition model has been recently described that allows for the evaluation of the antagonist potential of FP receptor antagonists (Chollet, et al., *BMC Pregnancy and Childbirth* 2007, 7 (Suppl 1): S16, incorporated herein by reference in its entirety). Briefly, pregnant CD1 mice at day 14 or 17 are treated with sc RU486 at 2.5 mg/kg in 5 mL. The animals are then treated (orally, sc, im, or ip) with the putative agonist, and its ability to prevent preterm parturition is measured.

Example 15

FP receptor antagonists are tested for their potential to inhibit pigmentation of the skin or hair, or to lighten skin or hair, using a minolta meter CM-SA (Konica Minolta Sensing Americas, Inc., Ramsey, N.J.). Used in combination with a Konica Minolta spectrophotometer, the CM-SA enables highly accurate measurement of skin color simultaneously with a numerical display of the Melanin Index, Hb (Hemoglobin) Index, and Hb SO2 (Hemoglobin oxygen saturation) Index (%). Measurement is performed by simply placing the head of spectrophotometer against the skin of the subject and pressing the button. Measurement by just applying light to the face, arm, or other desired part of the body will not put undue stress on the examinees. After a treatment regimen as described in Examples 16-20 below, the melanin index shows lightening of the skin or inhibition of pigmentation. A delta L value (change in the value of L) of 5 points is typically evidence of significant skin lightening.

Example 16

A simple topical composition is prepared by combining the following components utilizing conventional mixing techniques:

| Component | Percent by Weight of Composition |
| --- | --- |
| FP antagonist | 0.05% |
| ethanol | 85% |

This composition is applied twice daily to the skin or hair as appropriately needed, in an amount sufficient to deposit about 0.5 µg/cm² skin for six months. The composition inhibits pigmentation of the skin or hair and/or lightens the skin or hair.

Example 17

A cream is prepared by combining the following components using conventional mixing techniques:

| Component | Percent by Weight of Composition |
| --- | --- |
| Water phase | |
| U.S. Pharmacopia grade H₂O | 63.03 |
| Disodium EDTA | 0.13 |
| Glycerin | 3.00 |
| Methyl paraben | 0.25 |
| Oil phase | |
| propylene glycol dicaprylate/dicaprate | 3.00 |
| glyceryl stearate | 4.00 |
| cetyl alcohol | 1.00 |
| stearyl alcohol | 1.00 |
| ethoxylated cetyl stearyl alcohol | 1.5 |
| propyl paraben | 0.1 |
| Preservative phase | |
| U.S. Pharmacopia hrade H₂O | 1.49 |
| butylene glycol | 1.50 |
| benzyl alcohol | 0.5 |
| Active solution | |
| FP antagonist | 0.3% |
| water | 17% |

The first three phases are mixed with the active solution. The composition is applied to the skin as appropriately needed once every other day for two months to lighten the skin.

Preferred compounds are tested using this formulation in the pigmented guinea pig to determine their in vivo efficacy in a composition. On each guinea pig from two to six treatment sites (typically 16 cm² each) are treated topically with compounds formulated in the vehicle (100 µL of 0.1-3% active, 5 times per week for up to 6 weeks) with appropriate placebo and untreated control patches on the same animal. The animals are visually and instrumentally graded for erythema and skin lightening. It is determined that the preferred compounds lightened skin without pigmentation rebound or appreciable irritation.

Based on these results, in application to a human face (approximately 300 cm²), for example, about 1-2 g (or 1-2 mL) of cream is used.

Example 18

A nonionic oil-in-water emulsion is prepared by combining the following components using conventional mixing techniques:

| Component | Percent by Weight of Composition |
|---|---|
| deionized water | 78.83 |
| propylene glycol | 3.00 |
| octyl methoxycinnamate | 7.50 |
| cetyl alcohol | 2.50 |
| stearyl alcohol | 2.50 |
| laureth 23 | 2.00 |
| C12-C15 alcohols benzoate | 2.00 |
| EDTA | 0.37 |
| methyl paraben | 0.20 |
| propyl paraben | 0.10 |
| FP antagonist | 1.00 |

The composition is applied to the skin or hair as appropriately needed once a day for four months. Use of an amount sufficient to deposit about 15 µg of the active per cm² skin or hair is appropriate. The composition inhibits pigmentation of the skin or hair and/or lightens the skin or hair.

Example 19

A sunscreen composition is prepared by combining the following components utilizing conventional mixing techniques:

| Component | Percent by Weight of Composition |
|---|---|
| polypropylene glycol 15 stearyl ether | 15.00 |
| sorbitan oleate | 2.00 |
| octyl methoxy cinnamate | 7.50 |
| propyl paraben | 0.15 |
| butylated hydroxyl toluene | 0.05 |
| cyclomethicone | 20.00 |
| sesame oil | 5.00 |
| mineral oil (Blandol) | 50.30 |
| FP antagonist | 0.07 |

The above composition is applied to the skin twice a week for five months. Use of an amount sufficient to deposit 100 µg of the active per cm² skin is appropriate. The composition inhibits pigmentation of the skin and/or lightens the skin.

Example 20

A composition is prepared by combining the following components utilizing conventional mixing techniques:

| Component | Percent by Weight of Composition |
|---|---|
| deionized water | 89.63 |
| EDTA | 0.37 |
| FP antagonist | 0.01 |

The above composition is applied once to the skin or hair as appropriately needed every three days for three months. Use of an amount sufficient to deposit 120 µg of the active per cm² skin or hair is appropriate to lighten hyperpigmented regions.

Further information is found in the following references, and each reference is incorporated by reference herein in its entirety:

1. Jimenez J J, Roberts S M, Mejia J, Mauro L M, Munson J W, Elgart G W, et al. Prevention of chemotherapy-induced alopecia in rodent models. *Cell Stress Chaperones* 2008; 13(1):31-38.
2. Hussein A M, Jimenez J J. McCall C A, Yunis A A. Protection from chemotherapy-induced alopecia in a rat model. *Science* 1990; 249(4976): 1564-6.
3. Sredni B, Xu R H, Albeck M. Gafter U, Gal R, Shani A, et al. The protective role of the immunomodulator AS101 against chemotherapy-induced alopecia studies on human and animal models. *Int J Cancer* 1996; 65(1):97-103.
4. Jimenez J J, Wong G H W, Yunis A A. Interleukin 1 protects from cytosine arabinoside-induced alopecia in a rat model. *FASEB J* 1991; 5(10):2456-2458.
5. Hussein A M. Interleukin 1 protects against 1-beta-D-arabinofuranosylcytosine-induced alopecia in the newborn rat model. *Cancer Res* 1991; 51(12):3329-30.
6. Basarl A L, Morelli D, Menard S. Veronesi U, Colnaghi M I. Protection against doxorubicin-induced alopecia in rats by liposome-entrapped monoclonal antibodies. *FASEB J* 1994; 8(2):226-230.
7. Paus R, Handjiski B, Eichmuller S, Czarnetzki B M. Chemotherapy-induced alopecia in mice—induction by cyclophosphamide, inhibition by cyclosporine-A, and modulation by dexamethasone. *Am J Pathol* 1994; 144(4):719-734.
8. Hussein A M, Stuart A, Peters W P. Protection against chemotherapy-induced alopecia by cyclosporine A in the newborn rat model. *Dermatology* 1995; 190(3):192-196.
9. Shirai A, Tsunoda H, Tamaoki T, Kamiya T. Topical application of cyclosporin A induces rapid-remodeling of damaged anagen hair follicles produced in cyclophosphamide administered mice. *J Dermatol Sci* 2001; 27(1):7-13.
10. Hussein A M. Protection against cytosine arabinoside-induced alopecia by minoxidil in a rat animal model. Int J Dermatol 1995; 34(7):470-3.
11. Jimenez J J, Yunis A A. Protection from 1-beta-D-arabinofuranosylcytosine-induced alopecia by epidermal growth factor and fibroblast growth factor in the rat model. *Cancer Res* 1992: 52(2):413-5.
12. Danilenko D M, Ring B D, Yanagihara D, Benson W, Wiemann B, Starnes C O, et al. Keratinocyte growth factor is an important endogenous mediator of hair follicle growth, development, and differentiation: normalization of the nulnu follicular differentiation defect and amelioration of chemotherapy-induced alopecia. *Am J Pathol* 1995; 147(1):145-54.
13. Botchkarev V A, Komarova E A, Siebenhaar F, Botchkareva N V, Komarov P G, Maurer M, at al. p53 is essential for chemotherapy-induced hair loss, *Cancer Res* 2000; 80(18):5002-5006.
14. Davis S T, Benson B G, Bramson H N, Chapman D E, Dickerson S H, Dold K M, at al. Prevention of chemotherapy-induced alopecia in rats by CDK inhibitors. *Science* 2001; 291(5501):134-137.
15. Davis S T, Benson B G, Bramson H N, Chapman D E, Dickerson S H, Dold K M. et al. Retraction. *Science* 2002; 298(5602):2327.
16. Tsuda T, Ohmori Y, Muramatsu H, Hosaka Y, Takiguchi K, Saitoh F, at al. Inhibitory effect of M50054, a novel inhibitor of apoptosis, on anti-Fas-antibody-induced hepatitis and chemotherapy-induced alopecia. *Eur J Pharmacol* 2001: 433(1):37-45.
17. Jimenez J J, Haung H S, Yunis A A. Treatment with ImuVert/N-acetylcysteine protects rats from cyclophosphamide/cytarabine-induced alopecia. *Cancer Invest* 1992; 10(4):271-6.
18. Olsen E A (editor): *Disorders of Hair Growth: Diagnosis and Treatment*. New York, McGraw-Hill. 2003, and references cited therein.

We claim:

1. A method of inhibiting a condition selected from the group consisting of chemotherapy-related hair loss and radiation-related hair loss, the method comprising administering to a subject a safe and effective amount of a compound selected from the group consisting of:

Formula I and Formula II:

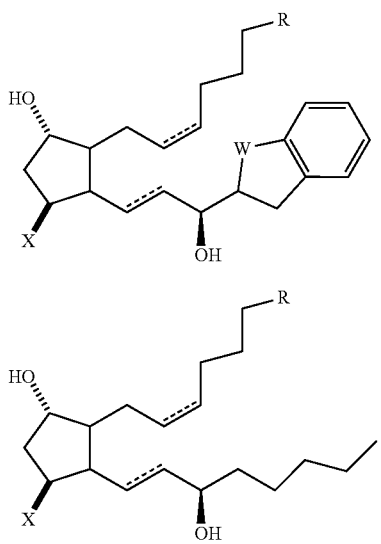

wherein R is selected from the group consisting of $CO_2H$, $C(O)NHOH$, $CO_2R_1$, $CH_2OH$, $S(O)_2R_1$, $C(O)NHR_1$, $P(O)(OR_1)R_2$, $C(O)NHS(O)_2R_1$, and tetrazole;

$R_1$ and $R_2$ are independently selected from the group consisting of a hydrogen atom, monovalent hydrocarbon groups, substituted monovalent hydrocarbon groups, aromatic groups, substituted aromatic groups, carbocyclic groups, substituted carbocyclic groups, heterogeneous groups, substituted heterogeneous groups, heterocyclic groups, substituted heterocyclic groups, heteroaromatic groups, and substituted heteroaromatic groups;

W is —$CH_2$—, —O—, or —$S(O)_2$—; and

X is halogen, lower alkyl, alkoxy, or hydrogen;

wherein the compound inhibits hair growth, thereby making the hair less susceptible to the negative effects of chemotherapy or radiation, and thereby inhibiting a condition selected from the group consisting of chemotherapy-related hair loss and radiation-related hair loss.

2. The method of claim 1, wherein the condition is chemotherapy-related hair loss.

3. The method of claim 1, wherein the condition is radiation-related hair loss.

4. The method of claim 1, wherein the compound is administered prior to chemotherapy or radiation, and wherein the compound arrests anagen hair growth prior to chemotherapy or radiation, thereby inhibiting hair growth prior to chemotherapy or radiation and rendering the subject less susceptible to chemotherapy-related hair loss or radiation-related hair loss.

5. The method of claim 1, wherein $R_1$ and $R_2$ are selected from the group consisting of $CH_3$, $C_2H_5$, and $C_3H_7$.

6. The method of claim 1, wherein R is selected from the group consisting of $CO_2H$, $CO_2CH_3$, $C(O)NHC_2H_5$, $CO_2C_2H_5$, $CO_2C_3H_7$, $CO_2C_4H_9$, $CO_2C_3H_7O_2$, and $C(O)NHS(O)_2R_1$.

7. The method of claim 1, wherein X is methoxy, methyl, or halogen.

8. The method of claim 7, wherein X is F.

9. The method of claim 1, wherein the compound is selected from the group consisting of 11-deoxy-16-fluoro $PGF_{2\alpha}$ analog,

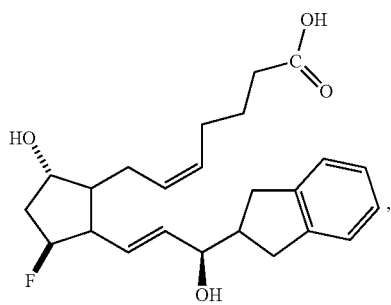

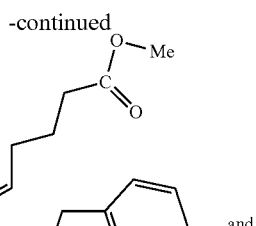
, and

10. The method of claim 1, wherein the compound arrests anagen hair growth, thereby inhibiting proliferation of hair follicle matrix cells, making hair less susceptible to the negative effects of cytotoxic agents or radiation that result in hair loss.

11. The method of claim 1, wherein the compound is administered to the subject topically.

12. The method of claim 1, wherein the compound is applied topically to the scalp, eyebrows, or eyelashes of the subject.

13. The method of claim 1, wherein the compound is formulated into a composition selected from the group consisting of shampoo and body wash.

* * * * *

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: Xaa = citrulline

<400> SEQUENCE: 1

Ile Leu Gly His Xaa Asp Tyr Lys
1               5
```